US012509379B2

(12) United States Patent

Pacheco-Ruiz et al.

(10) Patent No.: US 12,509,379 B2

(45) Date of Patent: Dec. 30, 2025

(54) GRANULAR SLUDGE REACTOR SYSTEM COMPRISING AN EXTERNAL SEPARATOR

(71) Applicant: Veolia Water Solutions & Technologies Support, Saint Maurice (FR)

(72) Inventors: Santiago Pacheco-Ruiz, Maassluis (NL); Thierry Alphonse Arnaud, Le Thor (FR); Jeronimus Gerardus Maria Van Der Lubbe, Rijswijk (NL); Hendrik Richard Paul La Vos, Delft (NL)

(73) Assignee: Veolia Water Solutions & Technologies Support, Saint Maurice (FR)

(*) Notice: Subject to any disclaimer, the term of this patent is extended or adjusted under 35 U.S.C. 154(b) by 520 days.

(21) Appl. No.: 17/800,443

(22) PCT Filed: Feb. 22, 2021

(86) PCT No.: PCT/EP2021/054343

§ 371 (c)(1),
(2) Date: Aug. 17, 2022

(87) PCT Pub. No.: WO2021/165541

PCT Pub. Date: Aug. 26, 2021

(65) Prior Publication Data

US 2023/0072206 A1 Mar. 9, 2023

(30) Foreign Application Priority Data

Feb. 21, 2020 (EP) .................................... 20158852

(51) Int. Cl.

*C02F 3/28* (2023.01)
*C02F 1/66* (2023.01)

(Continued)

(52) U.S. Cl.

CPC .............. *C02F 3/2846* (2013.01); *C02F 1/66* (2013.01); *C02F 3/2893* (2013.01); *C12M 21/04* (2013.01);

(Continued)

(58) Field of Classification Search

CPC ........ C02F 3/2846; C02F 1/66; C02F 3/2893; C02F 2103/28; C02F 2103/32;

(Continued)

(56) References Cited

U.S. PATENT DOCUMENTS 6,328,892 B1 12/2001 Jones
2018/0093910 A1* 4/2018 Kluit .................... C02F 3/2813

(Continued)

FOREIGN PATENT DOCUMENTS

CN 1699218 A 11/2005
CN 204224316 3/2015

(Continued)

OTHER PUBLICATIONS

Machine-generated English translation of CN 208617478, generated on Dec. 6, 2024.*

(Continued)

*Primary Examiner* — Fred Prince

(74) *Attorney, Agent, or Firm* — Hoffmann & Baron, LLP

(57) ABSTRACT

A method for treating an aqueous fluid comprising a biodegradable organic substance in an installation comprising an upflow bioreactor containing a sludge bed, said sludge bed comprising biomass, an external separator, and a conditioning tank, the method comprising: treating the fluid in the conditioning tank; feeding the treated fluid into a lower part of the bioreactor and forming biogas; withdrawing the fluid from an upper part of the bioreactor, which withdrawn fluid comprises biomass; feeding the aqueous fluid withdrawn from the upper part of the bioreactor into the external (Continued)

separator wherein the aqueous fluid comprising the biomass is separated into a liquid phase, and a fluid phase enriched in biomass; returning said fluid phase enriched in biomass from the external separator to the bioreactor; and returning a part of said liquid phase to the conditioning tank.

23 Claims, 11 Drawing Sheets

(51) Int. Cl.

| | |
|---|---|
| ***C12M 1/00*** | (2006.01) |
| ***C12M 1/107*** | (2006.01) |
| ***C12M 1/26*** | (2006.01) |
| *C02F 103/28* | (2006.01) |
| *C02F 103/32* | (2006.01) |
| *C02F 103/34* | (2006.01) |

(52) U.S. Cl.
CPC ............ *C12M 23/58* (2013.01); *C12M 29/18* (2013.01); *C12M 33/22* (2013.01); *C02F 2103/28* (2013.01); *C02F 2103/32* (2013.01); *C02F 2103/325* (2013.01); *C02F 2103/327* (2013.01); *C02F 2103/343* (2013.01); *C02F 2201/007* (2013.01); *C02F 2203/002* (2013.01); *C02F 2203/006* (2013.01); *C02F 2209/02* (2013.01); *C02F 2209/06* (2013.01); *C02F 2301/046* (2013.01); *C02F 2301/10* (2013.01); *C02F 2303/14* (2013.01); *Y02E 50/30* (2013.01)

(58) Field of Classification Search
CPC .......... C02F 2103/325; C02F 2103/327; C02F 2103/343; C02F 2201/007; C02F 2203/002; C02F 2203/006; C02F 2209/02; C02F 2209/06; C02F 2301/046; C02F 2301/10; C02F 2303/14; C12M 21/04; C12M 23/58; C12M 29/18; C12M 33/22; Y02E 50/30
USPC .......................... 210/605, 608, 609, 259, 260
See application file for complete search history.

(56) References Cited

U.S. PATENT DOCUMENTS

| | | | | |
|---|---|---|---|---|
| 2018/0334401 | A1* | 11/2018 | Leitner | C02F 3/2866 |
| 2020/0277210 | A1* | 9/2020 | Frankin | C12M 29/24 |
| 2021/0331958 | A1* | 10/2021 | Pacheco-Ruiz | C02F 3/2846 |

FOREIGN PATENT DOCUMENTS

| | | | | |
|---|---|---|---|---|
| CN | 204897526 | U | | 12/2015 |
| CN | 205442786 | U | * | 8/2016 |
| CN | 208617478 | | | 3/2019 |
| EP | 1408008 | | | 4/2004 |
| EP | 2590900 | | | 5/2013 |
| EP | 3613709 | | | 2/2020 |
| WO | 2004035485 | A1 | | 4/2004 |
| WO | WO2012005592 | | | 1/2012 |

OTHER PUBLICATIONS

Machine-generated English translation of EP 1408008, generated on Dec. 6, 2024.*

Machine-generated English translation of EP 2590900, generated on on Jun. 7, 2025.*

Halfor AB, Dissolved Air Floatation (DAF)—What is it and how does it work (2019), YouTube, https://www.youtube.com/watch?v=GOh5ZDHUI38.*

Machine-generated English translation of CN 205442786, generated on Sep. 22, 2025.*

* cited by examiner

GRANULAR SLUDGE REACTOR SYSTEM COMPRISING AN EXTERNAL SEPARATOR

This application claims priority from International Application No. PCT/EP2021/054343, filed on Feb. 22, 2021, which claims priority from European Patent Office application number EP 20158852.2, filed on Feb. 21, 2020, each of which is incorporated herein in its entirety.

TECHNICAL FIELD

The invention relates to a method for treating an aqueous fluid, whereby biogas is produced in an installation comprising a bioreactor. The invention further relates to an installation suitable for carrying out such a method.

DESCRIPTION OF THE PRIOR ART

Biological treatment of aqueous fluids, such as wastewater, uses active biomass (microorganisms, such as bacteria and/or archaea) to convert the pollutants (organic substances) to harmless components.

Basically there are two types of processes. For so-called anaerobic treatment (without oxygen) a consortia of anaerobic micro-organisms convert pollutants substantially to biogas.

In aerobic treatment, the pollutants are reduced under aerobic (with oxygen) conditions for a great extend to new micro-organisms (surplus sludge) which needs then to be separated from the treated wastewater and processed separately.

Anaerobic sludge bed reactor systems utilise anaerobic microorganisms to convert pollutants in aqueous fluids to biogas. These anaerobic bacteria mainly grow in aggregates, often referred to as granular biomass. The systems are often characterised by low net biomass production (typically 2-4% of converted COD) as a result of the low net yield of anaerobic microorganisms involved.

This is on one hand a big advantage, as the excess biomass developed in wastewater treatment systems has to be disposed as a solid waste, at significant cost, but it makes on the other hand a sensitive aspect to retain/maintain sufficient active biological sludge in the treatment system (reactor).

The method of retaining biomass in anaerobic treatment reactors can be done in various ways. The immobilization of biomass on a fixed or mobile carrier is one method to uncouple liquid retention time from biomass retention time. A better and preferred method however is to make use of mainly granulated biomass as applied in Upflow Anaerobic Sludge Blanket (UASB) reactors, Granular Sludge Bed reactors and IC reactors, see e.g. WO 2007/078195, Frankin R. J. (2001). Full scale experiences with anaerobic treatment of industrial wastewater. *Wat Sci. Tech.,* 44(8), 1-6).

Granular sludge bed (GSB) reactors, such as Expanded Granular Sludge Bed (EGSB) reactors are commonly used reactors for the treatment of wastewater of for example the food processing and beverages industries, distilleries, pharmaceutical industries and pulp and paper mills. Such wastewater typically contains large amounts of organic pollutants that need to be removed before the water can be reused or discarded.

In a typical (E)GSB reactor, wastewater is introduced into a lower part of an upflow bioreactor. Subsequently the water flows upwards through a granular sludge bed that comprises microorganisms which breakdown organic waste, present in the wastewater, whereby biogas—in particular methane and carbon dioxide—is formed which methane can in turn be used as a green energy source, for example to provide energy. Efficiency of high-rate anaerobic reactors (expanded granular sludge bed) is strongly dependent on good sludge bed expansion, liquid turbulence and high flow rate as these promote good mass transfer, less clogging and less short-circuiting (Van Lier, J. B., van der Zee, F. P., Frijters, M. E. Ersahin, Rev Environ Sci. Biotechnol. 2015, 14(4), 681-702).

Key to an efficient process is an efficient separation of the biomass (granules), water (effluent) and biogas, in other words, being able to remove the effluent and biogas whilst keeping the biomass in the system to achieve a net growth of granular biomass. There are several parameters that influence good separation of the liquid, solid and gas phase in GSB reactors, such as EGSB reactors.

As the skilled person knows, one important parameter to achieve such efficient separation is the settling behavior of the biomass. Good settling behavior of the granules is necessary to achieve efficient separation of the phases. Settling of the granules is influenced by several factors, such as the hydraulics or fluid dynamics (liquid and gas) inside the reactor and/or the presence and design of a three phase separator device inside the reactor (turbulent and laminar flows, turbulence and upflow velocities). Furthermore, settling behavior can depend on the composition of the sludge granule, such as the biomass content, and/or mineral fraction. For example sludge granules with a high inert fraction (any matter that is not biodegradable) could settle faster, but its degradation activity could be lower or any degradation activity could even be absent. Thus, inert sludge granules have the risk of not being able to expand and/or recirculated as a consequence of the biogas production and/or flow recirculation. Thus, in conventional systems, they will have a tendency to remain at the bottom of the reactor, thereby blocking the sludge extraction ports and causing major issues of operation.

On top of this, the settling behavior of the granules is affected by the presence of gas inside the granules. Biomass located at the bottom of the reactor is subject to a higher pressure than that at the top of the reactor due to the great height that GSB systems, in particular EGSB systems may have, typically between 15 m and 25 m, and consequently the pressure caused by the water column, which is typically 1.5-2.5 bars. Hence the gas inside the granules at the bottom of the reactor is compressed, resulting in a higher density of the granules, and therefore the granules settles faster.

Second, separating devices such as settlers are valuable tools towards achieving an improved separation of different phases and thereby enhancing the overall efficiency of the wastewater treatment process.

Efficient separation of the phases may further be enhanced by creating particular flows inside of the reactor that aid for example the settleability of biomass (by pushing the solids downward). Such flows may be introduced by the separation systems such as the tilted plates in internal settlers, may be caused by the solubility of carbon dioxide in water creating turbulence or may be caused by the mere movement of the phases due to a difference in density, e.g. sludge tends to move downwards by gravity, whereas biogas flows upwards.

An example of an EGSB reactor is described in WO 2007/078195. Further known is the BIOTHANE Biobed Advanced EGSB. This reactor has a three-phase separator, in a bioreactor and further comprises a conditioning tank. In the upper part of the bioreactor a tilted plate settler (TPS) is present, aiding the separation of biogas from effluent and biomass. In the lower part of the tilted plate settler a mammoth flow effect is created due to a difference in pressure beneath the tilted plate with respect to the top part of the plate, enabling a better separation of biogas and directing the settled biomass downwards.

EP 0 493 727 relates to a reactor for continuous mechanical and anaerobic biological purification, optionally having an external separation device, preferably a cyclone. The lower part of the reactor comprises a settling zone that is separated from the reactor with a bottom having perforations allowing passage of liquids whilst preventing passage of solids.

A drawback of this system is that sludge settles below the influent lines such that the interaction between wastewater and sludge is suboptimal, reducing the efficiency of the system.

WO2012/005592 aims to overcome this problem, by designing a reactor having a second settler placed on the bottom of the bioreactor where biomass is separated from the liquid effluent with higher efficiency, because the separation occurs at higher pressure. Fluid that has been separated from biogas in a tilted plate settler located in the upper part of the reactor is transported into this second settler through an external separator feed conduit. It is the present inventors finding that drawbacks of this system include:

- Lack of proper control of the recirculation in the reactor, particularly when biogas production is low or lacking, such as during start-up
- Huge potential for blockage of second settler placed on the bottom of the bioreactor
- Lack of accessibility of this separation chamber for maintenance; requiring complete emptying of the reactor if maintenance wants to be performed
- Difficult operation when there is no biogas production (start-up)

SUMMARY OF THE INVENTION

The inventors now surprisingly found a way to have a highly efficient process for treating an aqueous fluid that overcomes these drawbacks by not having a second settler located inside of the reactor. Instead, an external separation chamber is provided outside the bioreactor, usually prior to a return line to a conditioning tank configured for treating the aqueous fluid comprising biodegradable substance upstream of the bioreactor. However, in a specific embodiment, the installation according to the invention or used in a method according to the invention is without such conditioning tank.

Accordingly, the invention relates to a method for treating an aqueous fluid comprising a biodegradable organic substance in an installation comprising an upflow bioreactor (1) containing a sludge bed (57), said sludge bed (57) comprising biomass and an external separator (2), wherein the method comprises

- feeding the aqueous fluid into a lower part of the bioreactor, contacting the fed fluid with the biomass, thereby forming biogas from the biodegradable organic substance;
- withdrawing the fluid that has been contacted with the biomass from an upper part of the bioreactor, which withdrawn fluid comprises biomass;
- feeding the fluid comprising the biomass withdrawn from the upper part of the bioreactor into the external separator (2) comprising a separation chamber, preferably provided with tilted internals, wherein the fluid comprising the biomass is separated into a liquid phase, which has a reduced biomass content or is essentially free of biomass, and a fluid phase enriched in biomass.

Fluid phase enriched in biomass from the external separator (2) is subjected to a density reduction downstream of the external separator'. The density reduction provides a lifting effect of the fluid phase, providing at least part of driving force to create a fluid to flow. The fluid phase enriched in biomass is thereafter returned to the bioreactor, either whilst it still has a reduced density or after having been subjected to a treatment wherein the density is increased again. Alternatively or in addition the fluid phase enriched in biomass from the external separator is returned to the bioreactor making use of a venturi-injector.

The invention further relates to an installation for microbiologically treating an aqueous fluid comprising a biodegradable organic substance, wherein the installation comprises

- a bioreactor (1), the bioreactor comprising an outlet for biogas;
- an external separator (2) comprising a separation chamber provided with tilted internals, arranged to separate a liquid phase from a fluid phase comprising biomass, the external separator comprising an inlet (4) for an aqueous fluid connected to an inlet (5) of a conduit (6) for withdrawing an aqueous fluid from bioreactor (1), an outlet (7*a*) for aqueous fluid, an outlet (8) for a fluid enriched in biomass to an inlet (9) for the fluid enriched in biomass into the bioreactor (1) via a conduit (10); and
- at least one of (a) an injector configured to inject a fluid medium, in particular an expandable fluid medium, such as a gas or a (pressurized) liquid comprising dissolved gas or a (pressurized) liquefied gas, into the fluid enriched in biomass downstream of the external separator and (b) a venturi-injector configured to return fluid enriched in biomass from the external separator to the bioreactor, said venturi-injector having an internal constriction adapted to create a venturi-effect.

The installation according to the invention or used in a method according to the invention is thereby configured to generate at least part of the driving force for returning fluid phase enriched in biomass from the external separator to the bioreactor; in an advantageous embodiment this is accomplished by making use of a density reduction in the fluid phase that is returned to the bioreactor by generating a lift effect due to the density reduction (typically a gas lift effect) in the conduit for returning the fluid phase and/or in the bioreactor (see e.g. FIGS. 1-5). The density reduction causes an upward motion, typically by providing a gas phase in the fluid enriched in biomass that draws said fluid from the external separator into the bioreactor. Said fluid phase may be returned to the bioreactor whilst still having a reduced density, or may first be subjected to a step of increasing the density of said fluid phase, preferably to about the same density as before the density reduction treatment. If the fluid phase has been previously subjected to a density reduction by introducing a gas (to create a gas lift effect), said step to increase the density of said fluid phase usually involves removing at least part of the gas that has been introduced from the fluid phase.

In a further advantageous embodiment, which can be employed as an alternative or in combination with the density reduction, use is made of the venturi-effect (see e.g. FIG. 6).

For an advantageous lift-effect, the density reduction is generally achieved by introducing a gas phase into the fluid enriched in biomass that is returned from the external separator to the bioreactor. The gas phase can be introduced by injecting a gas phase in the passage way (10) for said fluid between the external separator (2) and the bioreactor (1). However, it is also possible to introduce a liquefied gas or gas dissolved in a liquid into the passage way for said fluid between the external separator and the bioreactor, which liquefied gas or dissolved gas expands or evaporates when introduced into the fluid enriched in biomass. This is generally achieved by introducing said liquefied gas or liquid comprising dissolved gas at a higher pressure than the pressure inside said passage way.

Applying the density reduction (such as by creating a gas lift effect) and/or the venturi-effect to the fluid phase enriched in biomass, in particular granular biomass from the external separator to the bioreactor is advantageous in particular in that the fluid recycle can be accomplished without the need of a mechanical pump through which the fluid enriched in biomass has to pass, or whilst using reduced mechanical pumping power. This is a major advantage, as the omission of a mechanical pump for pumping fluids with relatively high solids content reduces the risk of malfunctioning, e.g. due to clogging of blocking of moving parts of the pump. Another advantage of omitting a mechanical pump is that the net growth of biomass inside the bioreactor may be enhanced. Without wishing to be bound by theory, it is believed that the use of a mechanical pump for a pro-longed period of time is disadvantageous for the structure of biomass, in particular granular biomass inside the bioreactor, because of the shear stress caused by the pump onto the biomass. Hence, by omitting the use of a mechanical pump for at least a substantial part of the time, the structure of biomass, in particular granular biomass, inside the reactor may be enhanced, thereby improving the efficacy of the conversion of biodegradable substance to biogas. Further, it can offer energy savings.

Analogously, the venturi-effect can be employed to generate a fluid pressure difference in a fluid stream, whereby a another fluid (i.e. the fluid phase enriched in biomass coming from the external separator) is sucked into the fluid stream passing through a venturi-injector from a higher pressure inlet side to a lower pressure outlet side of the venturi-injector. Omitting (prolonged use of) a mechanical pump for returning fluid enriched in biomass as such or reducing the demanded power for a mechanical pump simplifies the installation/method and may enhance the structure of biomass, in particular granular biomass. It can further offer energy savings and/or reduced maintenance needs. In particular, when making use of the venturi-effect, said fluid phase enriched in biomass from the external separator is returned to the bioreactor via a venturi-injector (42) having a higher pressure inlet, a lower pressure outlet and a suction inlet, wherein aqueous fluid comprising a biodegradable substance to be treated in bioreactor enters the venturi-injector via said higher pressure inlet, the fluid phase enriched in biomass from the external separator enters the venturi-injector via said suction inlet and said fluid phase enriched in biomass, said aqueous fluid to be treated in the bioreactor leave the venturi-injector together via the lower pressure outlet and are fed to the bioreactor. A mechanical pump (11) may still be used, but is typically present in the conduit for aqueous fluid to be treated (16) upstream of the venturi-injector It has been found that the installation according to the invention is particularly suitable for the efficient separation of a gas-liquid-solid mixture into a gas phase, a liquid phase which is essentially free of granular biomass and a fluid phase enriched in solids, in particular enriched in particulate solids, in particular enriched in granular biomass. Although the installation is highly efficient its design is rather simple, in particular inside of the reactor only a limited number of technical devices are needed to enhance separation, which reduces the risk of malfunctioning and simplifies maintenance and cleaning. Important for a good separation is the external separator. The means to configure the installation to promote return of fluid enriched in biomass to the bioreactor via a lift effect or via a venturi-effect further contribute to an advantageous design.

Having an external separator allows for improved maintenance, improved start-up of the process and further enables the installation of the reactor in parts, i.e. allowing for an already existing system to be upgraded with an external separator, thereby improving the efficiency of the reactor.

The external separator, typically a settler having tilted internals, has been found particularly suitable to obtain a liquid phase which has a reduced granular biomass content compared to the fluid that is fed into the external separator. This is advantageously accomplished by allowing the granular biomass to settle. The settled granular biomass is then at least for a substantial part returned to the bioreactor (as part of the fluid phase enriched in granular biomass).

BRIEF DESCRIPTION OF THE DRAWINGS

Presently, the invention will be clarified on the basis of an exemplary embodiment and the drawings. In the drawings.

DETAILED DESCRIPTION OF THE INVENTION

Figure 1:
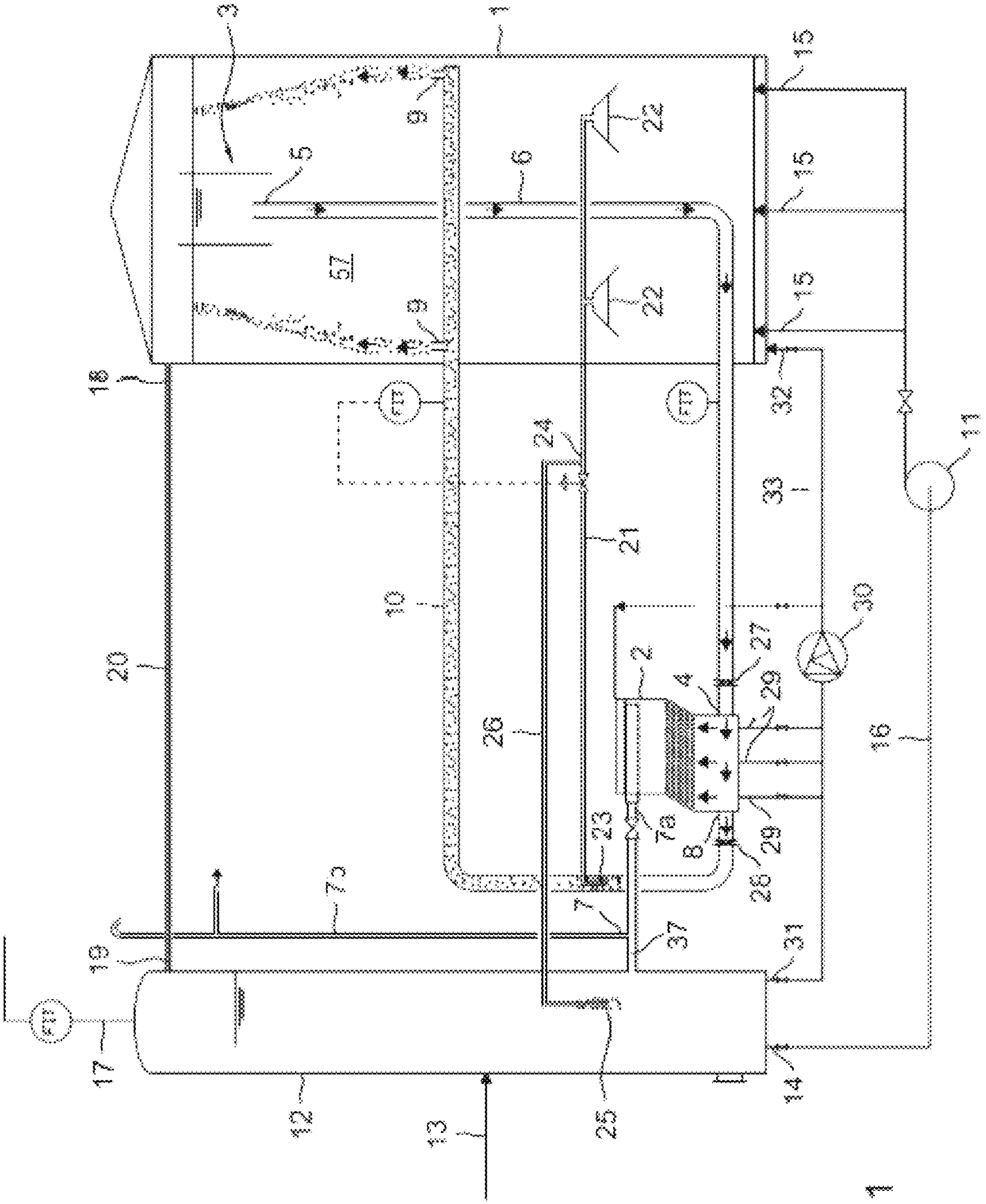
FIG. 1 schematically shows a general embodiment of an installation for use in the method for treating an aqueous fluid comprising a biodegradable organic substance.

FIG. 1 schematically shows a general set-up of an installation (for use in a process) according to the invention. It schematically shows how an aqueous fluid may be introduced via an inlet (13) into a preferably present conditioning tank (12), wherein the aqueous fluid (such as wastewater)

undergoes a conditioning step. The conditioning tank (12) further comprises an outlet for biogas (17), an outlet for the pre-conditioned fluid connected to an Influent Distribution System (IDS) (15) at or near the bottom of the bioreactor (1) via a conduit (16). Advantageously, the conduit (16) further comprises a recirculation pump (11) for the continuous and controlled recirculation of the fluid. The aqueous fluid passes through a sludge bed (57) comprising microorganisms that are capable of converting the biodegradable organic substance into biogas.

The presence of a recirculation pump (11) from the conditioning tank (12) to the bioreactor (1) enables controlled dilution of inhibitory compounds
constant flow rate to the EGSB
constant up flow velocity (independent to COD load rate)
better pH-control in CT due to of returned anaerobic effluent alkalinity"

In FIG. 1, the bioreactor (1) further comprises an internal baffle or deflector/separator (3), located in an upper part of the bioreactor (1) for removing biogas from the gas-aqueous fluid mixture and an outlet for biogas (18). The bioreactor (1) further comprises an internal feed conduit (6) with inlet (5) for an aqueous fluid comprising solids from which biogas has been separated that is connected to an inlet (4) of an external separator (2), for the separation of the solids from the liquid phase. The inlet (5) of conduit (6) is located under the baffle or deflector (3). The conduit (6) additionally comprising a valve (27) for isolating the external separator (2) from the installation in case of maintenance, reparation or replacement of external separator (2). Conduit (10) connects the outlet (8) of the external separator (2) with an inlet (9) for fluid enriched in solids from the bioreactor (1), in which conduit biogas injector (23) configured to introduce biogas into the fluid enriched in solids inside the conduit (10) is provided; and a biogas conduit (21) is provided between the biogas injector (23) and the biogas collection hoods inside the bioreactor (22). Conduit (10) also comprises a valve (28) for isolation of the external separator (2) from the installation in case of maintenance, reparation or replacement of the external separator (2).

The biogas conduit (21) in FIG. 1 further comprises a T-junction (24) for connecting the biogas conduit (21) to the biogas conduit (26) for introducing biogas, via inlet (25) into the conditioning tank (12) for mixing of the aqueous fluid inside of the conditioning tank.

FIG. 1 further shows means (7) to withdraw and recycle liquid phase from the external separator. It comprises an outlet (7*a*) to withdraw liquid phase with a reduced biomass content which may be essentially free of biomass) from the separator. From this outlet (7*a*) a withdrawal conduit (7*b*) can be provided from which the treated phase can exit the installation, and a recycle line (37) to return liquid phase into the conditioning tank (12).

The external separator (2), as shown in FIG. 1, also comprises inlets/outlets (29) connected to the inlet/outlet (31) of the conditioning tank (12) and inlet (32) of the bioreactor (1) via conduit (33). This conduit (33) comprises a pump (30) for returning sludge from the external separator to the bioreactor in case this is necessary. Additionally this conduit (together with isolation valves (27) and (28)) allow for recirculation of an aqueous fluid (usually acidic chemicals) for cleaning in place of the external separator—completely isolated of the reactor and conditioning tank by using the valves (2).

Further, the installation, as shown in FIG. 1, comprises a conduit (20) for biogas connecting an outlet for biogas (18) with an inlet for biogas (19) from the conditioning tank. Such provision can be provide to ensure that the pressure in the conditioning tank is essentially the same as in the bioreactor.

Figure 2:
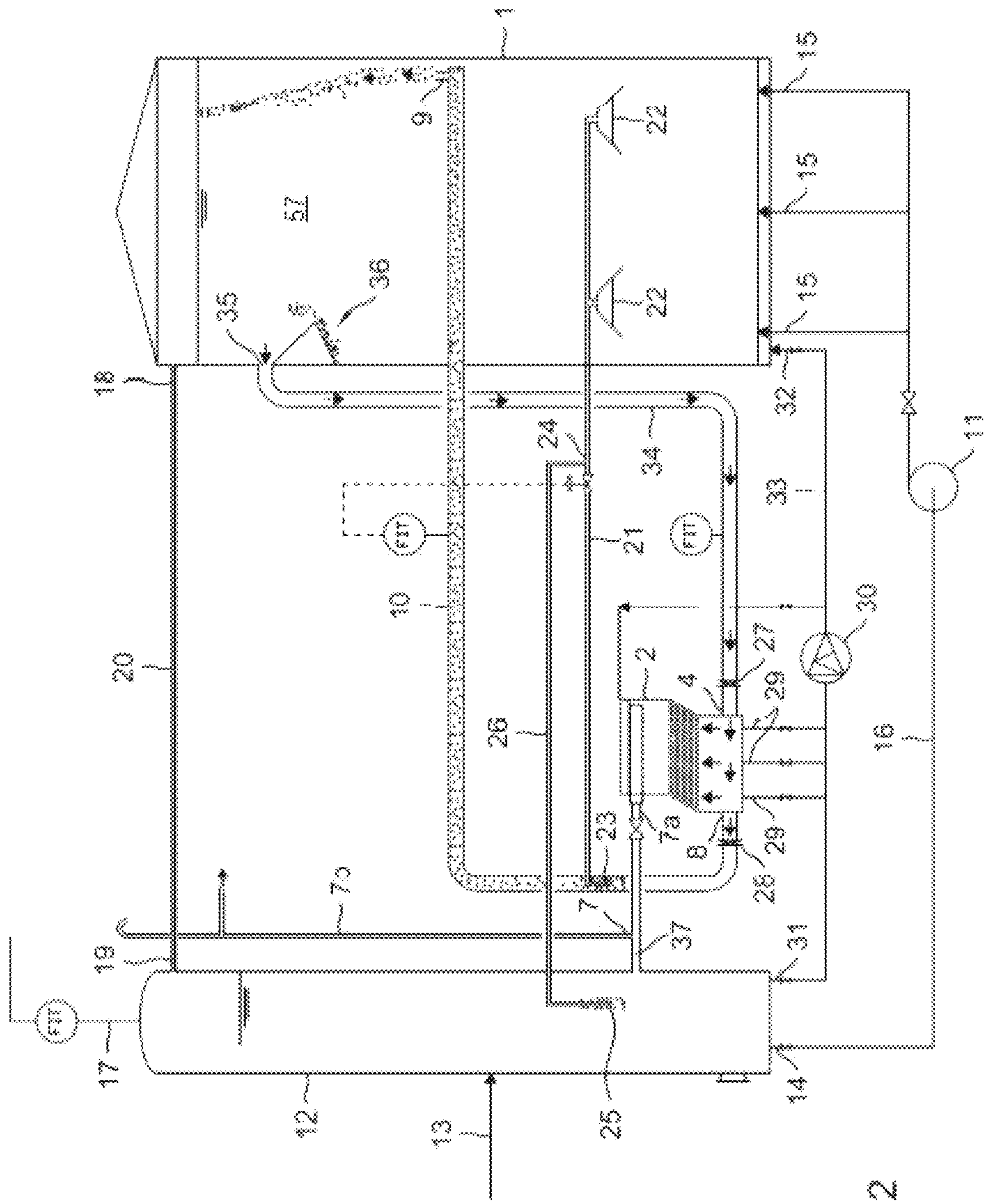
FIG. 2 schematically shows a second embodiment of an installation for use in the method for treating an aqueous fluid comprising a biodegradable organic substance.

FIG. 2 schematically shows a second set-up of an installation (for use in a process) according to the invention. For a detailed description of items see the description of FIG. 1. The bioreactor is provided with an external feed conduit (34) for feeding an aqueous fluid into the external separator (2). A deflector or baffle (36) is located in the bioreactor under the inlet (35) of the conduit (34) for directing the aqueous fluid comprising solids into the external feed conduit (34). This is a particularly preferred means for feeding aqueous fluid from the bioreactor to the external separator, amongst others from a low maintenance perspective.

Figure 3:
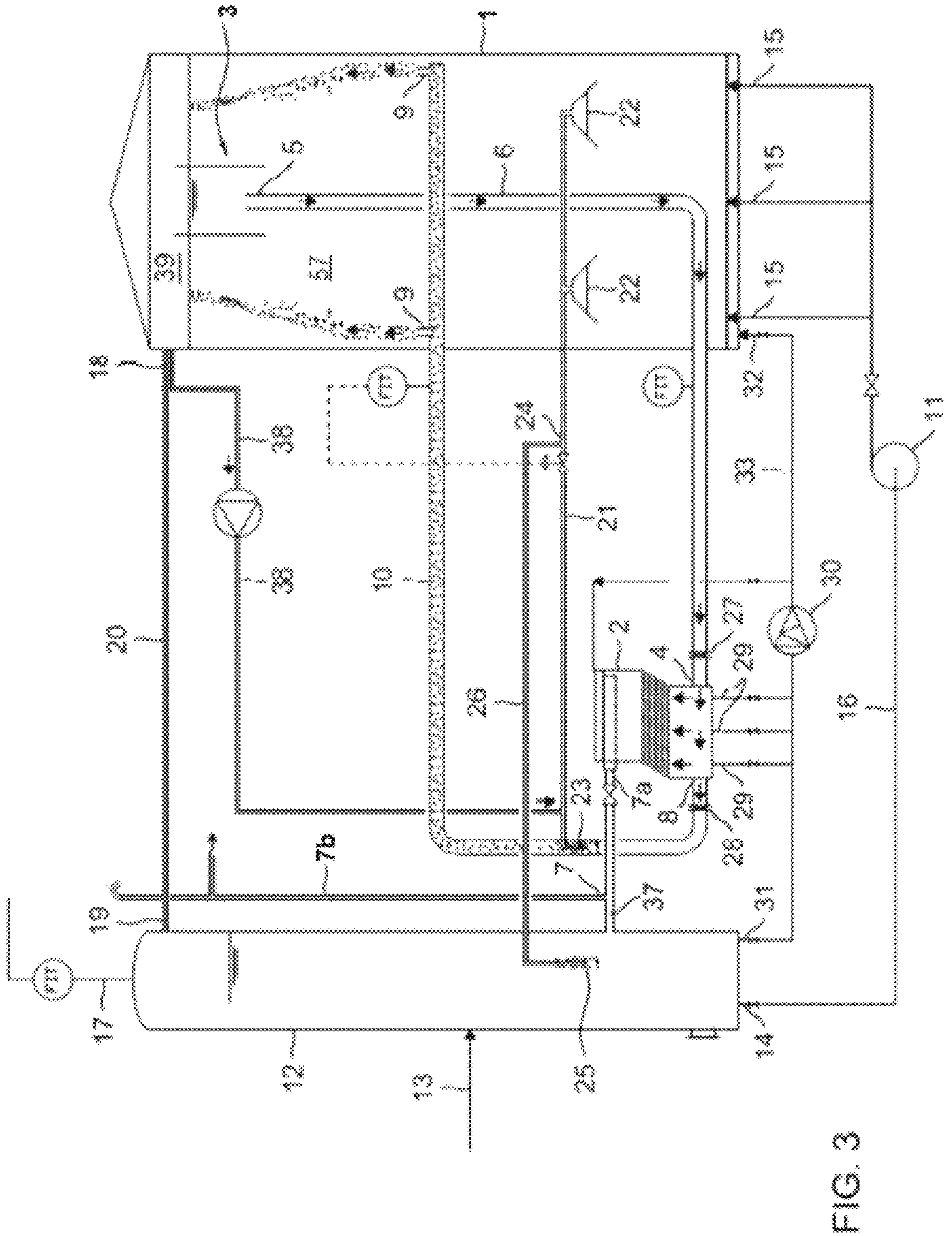
FIG. 3 shows a third embodiment that includes a provision to withdraw biogas for injection into the conduit for returning fluid enriched in biomass to the bioreactor.

FIG. 3 shows a further embodiment, which—compared to FIGS. 1&2—shows an additional provision to withdraw biogas for injection into the conduit (10) for returning fluid enriched in biomass to the bioreactor. The additional provision is a gas conduit (38) from the headspace (39) of the bioreactor (1) to the gas injector (23). It is configured to feed biogas from said headspace into conduit (10). Typically a mechanical pump or compressor or the like is present to cause a sufficient flow of biogas from the headspace (39) to the injector (23). This design is particularly suitable for use in a method according to the invention wherein biogas is taken from the headspace of the bioreactor and introduced into said fluid phase enriched in biomass downstream of the external separator (2), thereby reducing the density of said fluid enriched in biomass downstream of the external separator. Herewith the biogas contributes to or causes a gas-lift effect of the fluid that is recycled from the separator (2) to the bioreactor (1). Biogas from the headspace of the conditioning tank, if present, may also be used as an alternative or additional source of biogas to be introduced into the fluid enriched in biomass downstream of the external separator (2)) to create or contribute to a gas lift effect (not shown in FIG. 3).

Figure 4:
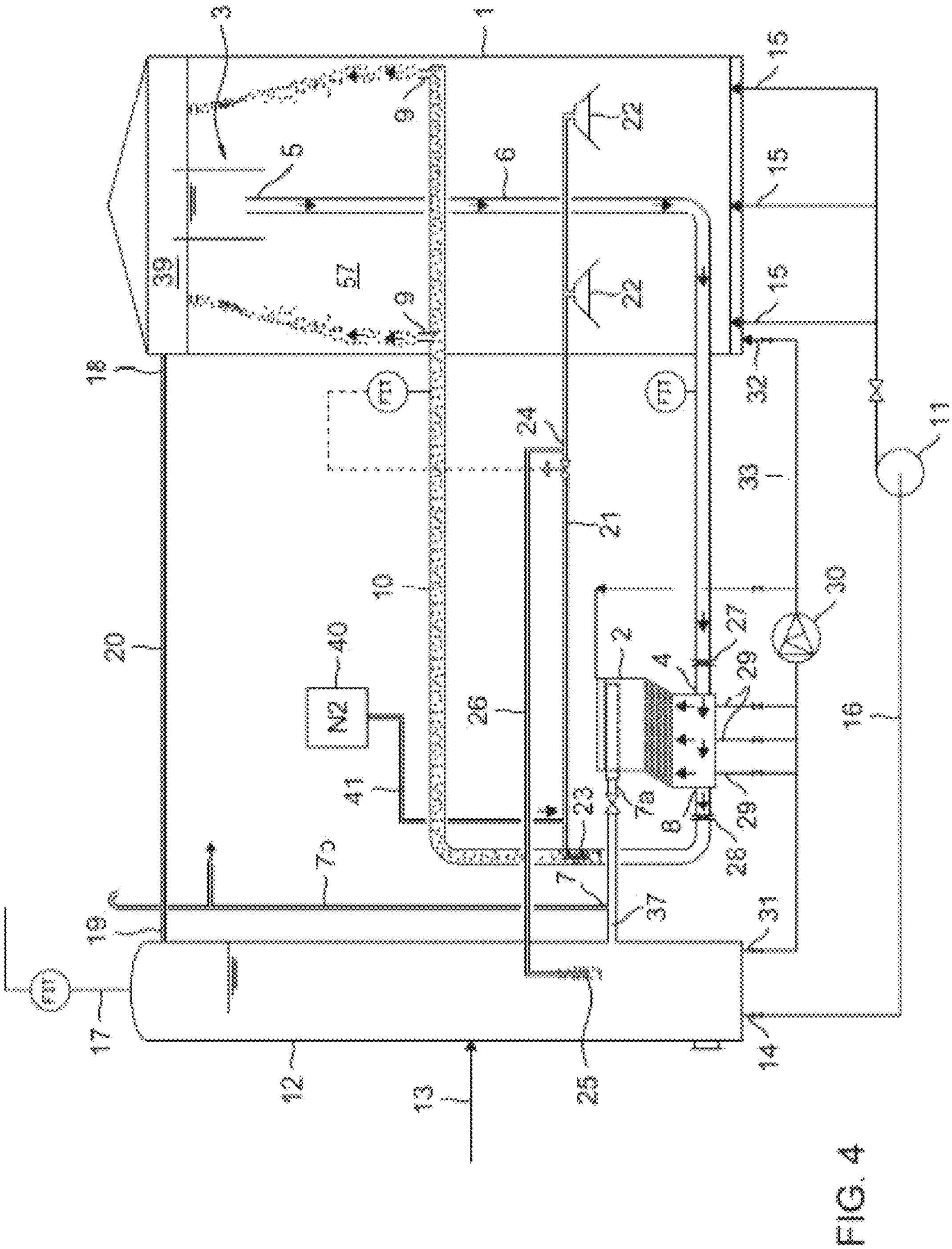
FIG. 4 schematically shows an alternative to the embodiment schematically shown in FIG. 3.

FIG. 4 schematically shows an alternative to the embodiment schematically shown in FIG. 3; both embodiments can be combined. Herein the injector (23) is connected via conduit (41) to an external source (40) for a fluid medium that can be used to create the gas lift effect in conduit (10). Such fluid medium preferably is a gas, in particular an inert gas such as nitrogen. Other particularly suitable gases include methane and carbon dioxide. The gas may be a mixture comprising any of these gasses. The fluid medium does not necessarily have to be injected as a gas phase. It may also be injected in a substantially liquid form, such as a (pressurized) liquefied gas or a (pressurized) liquid comprising dissolved gas, whereby at least a substantial part of the liquefied gas or dissolved gas expands/evaporates to create a reduction in density inside the passage way for fluid enriched in biomass between separator (2) and bioreactor (1), thereby creating a gas-lift effect.

In FIGS. 3 and 4 the features directed to fluid-medium (such as gas) injection into conduit (10) is shown in combination with the internal biogas collector (22) and a conduit (21) for feeding collected biogas to the fluid-medium injector (23). In such embodiment, the biogas from the headspace and/or the external source for creating a lift effect can be used to balance for fluctuations in gas flow from the biogas collector. Biogas from the headspace respectively an external gas source can e.g. be used as the sole fluid medium to generate a little effect. It can also be used to supplement gas from the biogas collector (22) inside the bioreactor, when there is insufficient gas flow from the biogas collector (22) to injector (23). This may in particular be the case during start-up of the installation. Further, this may be the case if the collector becomes (partially) clogged or if biogas flow inside the bioreactor from underneath the collectors into the collectors is relatively low. However, it is also possible to omit the biogas collector (22) in a method/installation wherein biogas from the headspace or an external source is used to create or contribute to the lift effect. Herewith the interior design of the bioreactor is simplified, which is advantageous because of reduced maintenance requirements. Such design is also advantageous for revamping existing bioreactors, because such design can be incorporated without needing to modify the internal of such reactor. A method/installation wherein headspace gas (FIG. 3) or external gas source (FIG. 4) is used for a lift effect, can also be employed in an installation having a bioreactor wherein a deflector or baffle (36) is located under the inlet (35) of the conduit (34) for directing the aqueous fluid comprising solids into the external feed conduit (34) (FIG. 2).

Figure 5:
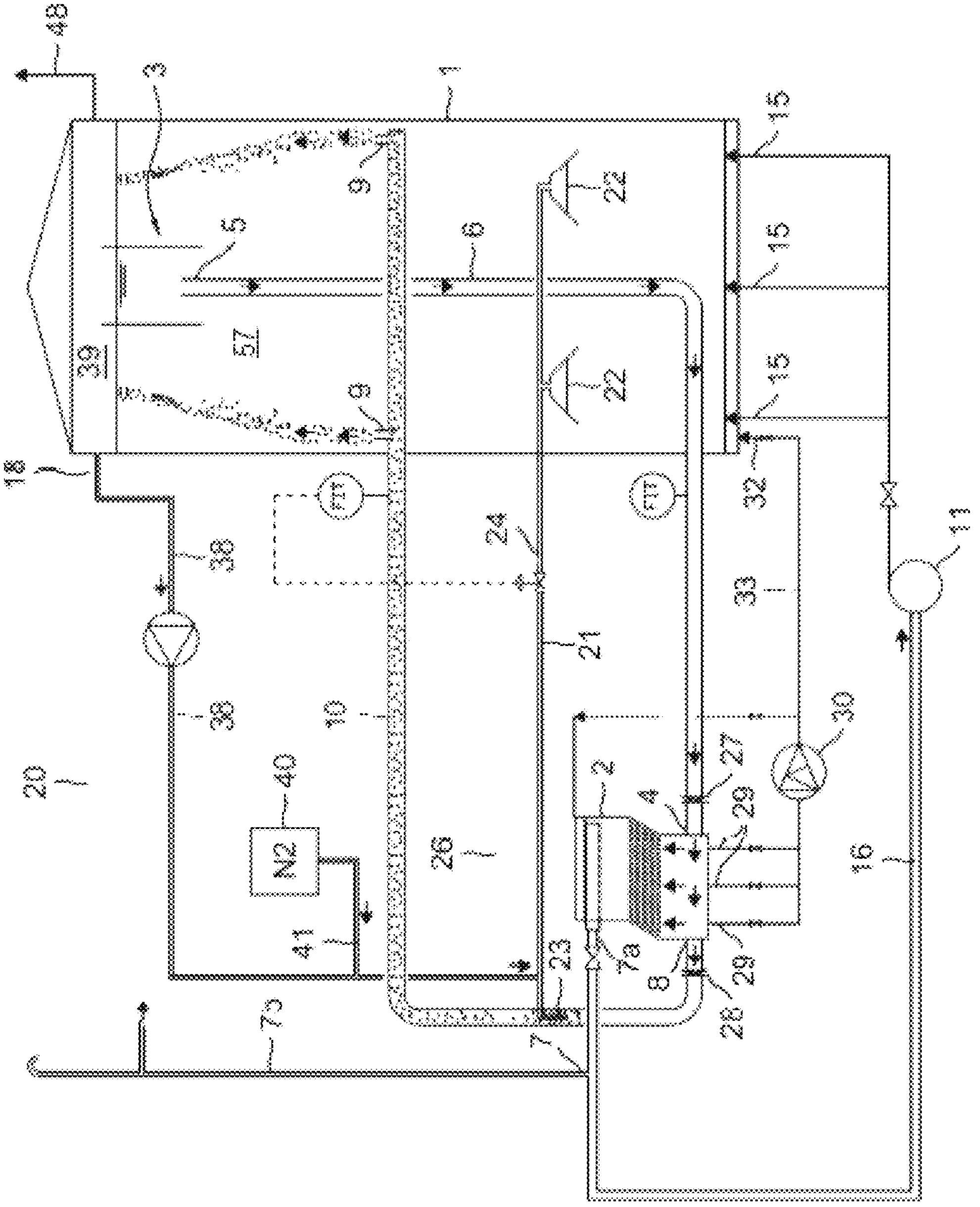
FIG. 5 schematically shows an installation according to the invention without a conditioning tank.

FIG. 5 schematically shows an installation according to the invention without a conditioning tank. It shows the injector (23) connected to each of the internal biogas collectors (22), the bioreactor's headspace (39) and the external source for a fluid medium for creating or contributing the lift effect. It is sufficient to have only one of these present; preferably the installation is at least configured to provide biogas from the headspace (39) of the bioreactor (1) to the injector (23) and/or to provide the external source for fluid medium for creating or contributing the lift effect. In this embodiment a biogas outlet (48) is typically provided in the headspace of the bioreactor, configured to let the biogas leave the installation; in an embodiment with a conditioning tank, such biogas outlet may also be present; in addition or alternatively (in case there is a passage way for biogas between the headspace of the bioreactor and conditioning tank present) it can be provided in the headspace of the conditioning tank (12).

Figure 8:
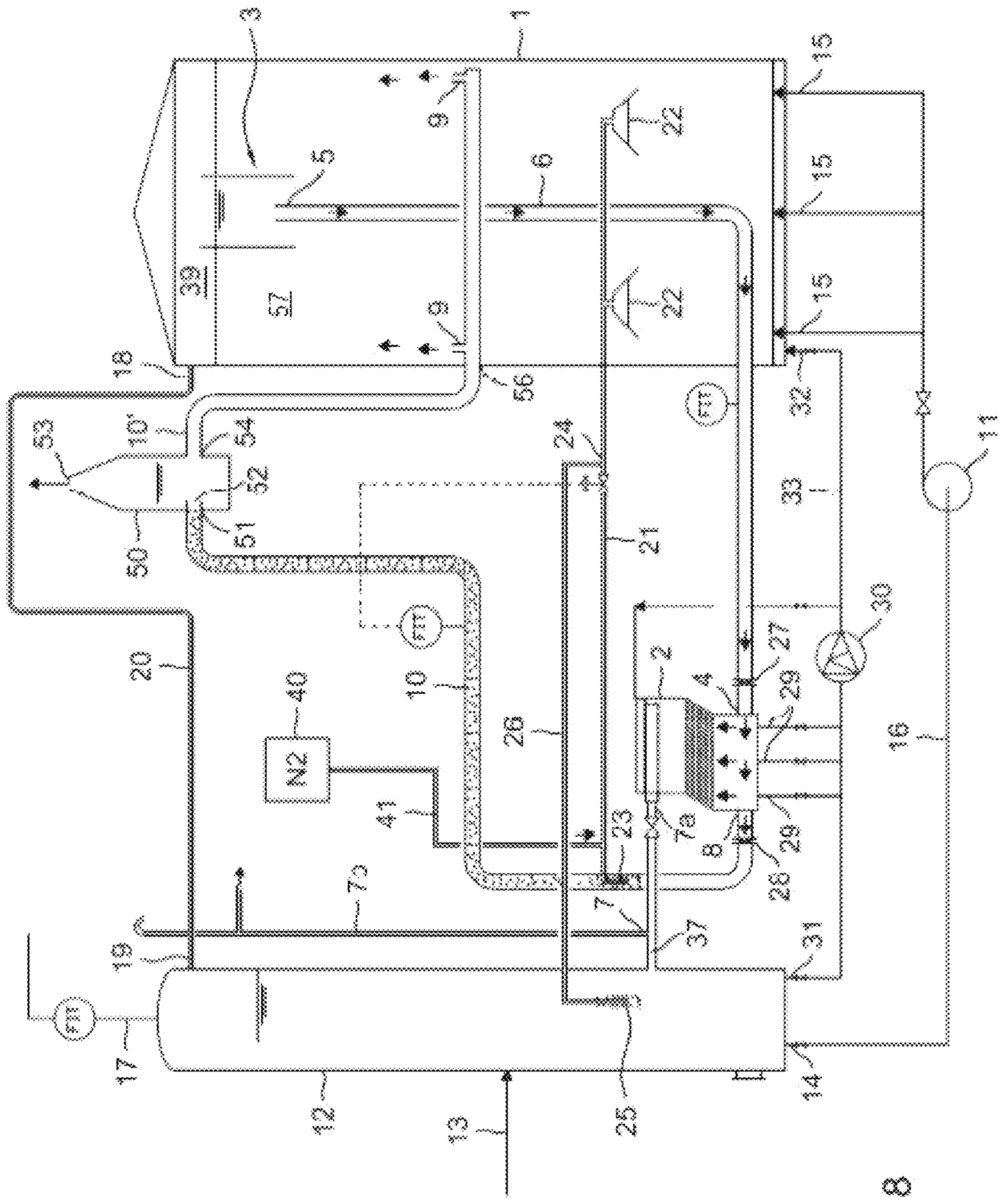
FIG. 8 schematically shows the features of the installation directed to separating gas from the fluid enriched in biomass prior to returning the fluid enriched in biomass to the bioreactor.

In FIG. 8 the features directed to separating gas from the fluid enriched in biomass, which has been subjected to a density reducing treatment, prior to returning the fluid enriched in biomass to the bioreactor, are shown. This embodiment may be combined with FIG. 4 or 5. It shows that a fluid-gas separator (50) is provided with an inlet (51), which inlet is connected to conduit (10) for a fluid enriched in biomass which has been subjected to a reduction of density, via outlet (52). The fluid-gas separator (50) is configured to separate the fluid into a gas phase and a fluid phase comprising biomass and is arranged relative to the bioreactor (1) such that, during use, the fluid level inside the fluid-gas separator (50) is at a higher level than the fluid level inside the bioreactor (1). Said fluid-gas separator further comprises an outlet (53) for discharging gas and an outlet (54) for a fluid comprising biomass. Said outlet (54) for a fluid comprising biomass is connected to an inlet (56) for returning the fluid comprising biomass to the bioreactor via conduit (10'). Herein said outlet (54) configured to discharge the returned mixture into the bioreactor is located higher than the injector configured to inject a fluid medium, and which outlet (54) configured to discharge the returned mixture into the bioreactor preferably is in a middle or lower part of the bioreactor.

Figure 9:
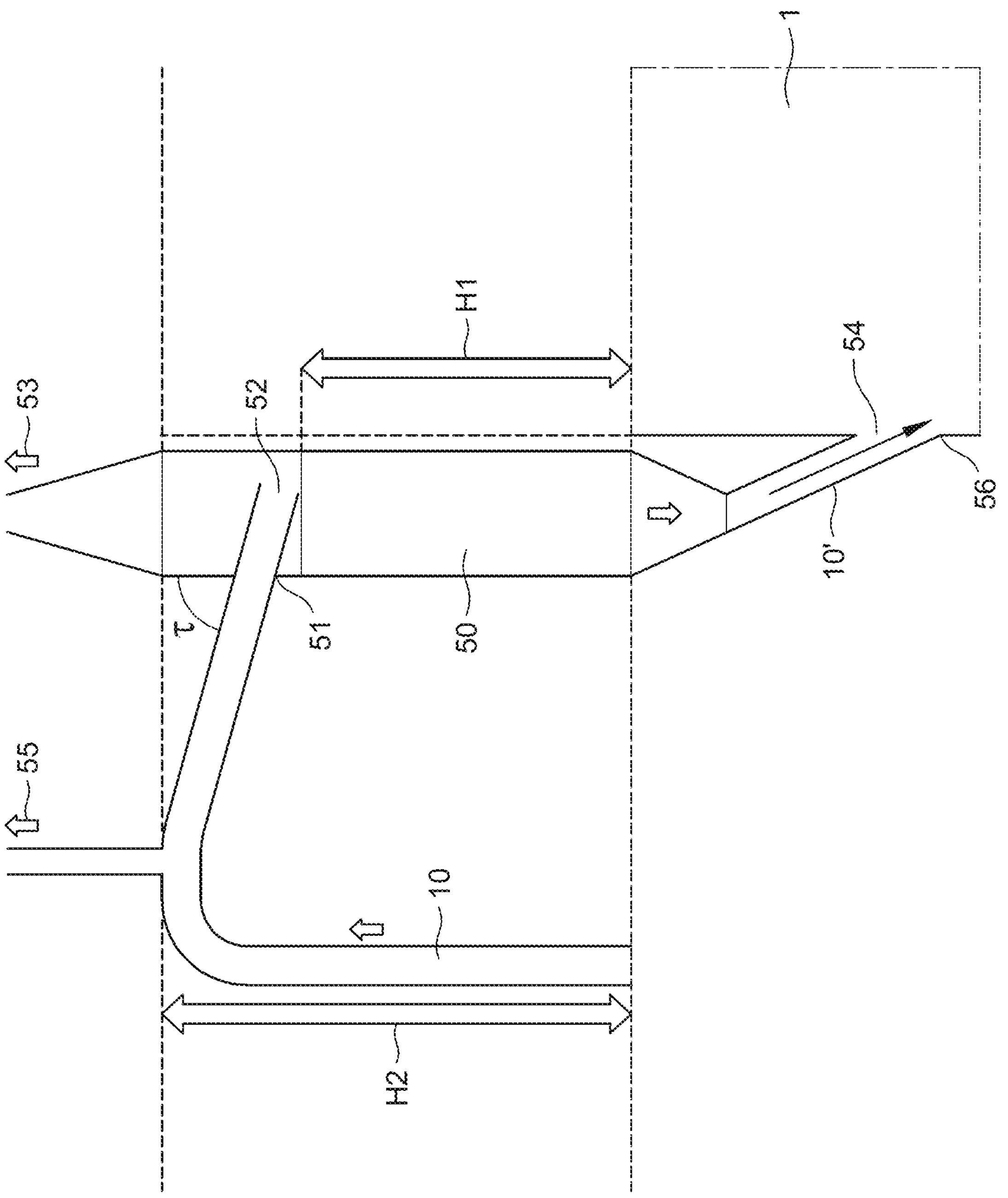
FIG. 9 schematically shows in detail a preferred embodiment of a fluid-gas separator for use in an installation.

An example of a preferred fluid-gas separator (50) which is particularly useful in an installation as shown in FIG. 8, is shown in FIG. 9. Herein conduit (10) is connected to the inlet of the fluid-gas separator under an angle tau, relative to the y-axis or vertical axis of the fluid-gas separator. Said conduit (10) is further provided with an outlet (55) for discharge of gas. Said outlet (52) is generally located at height h2, which is higher than the fluid level inside the bioreactor. Further, fluid-gas separator (50) is provided with an inlet (51) connected to an outlet of the conduit (10) and is configured such that, during use, the fluid enriched in biomass and comprising gas enters the fluid-gas separator (50) at height h1, which h1 is higher than the fluid level inside the bioreactor (1). Said fluid-gas separator is further provided with an outlet (53) configured to discharge gas from the fluid-gas separator and an outlet (54) configured to discharge the fluid comprising biomass into the bioreactor via conduit (10').

Figure 6:
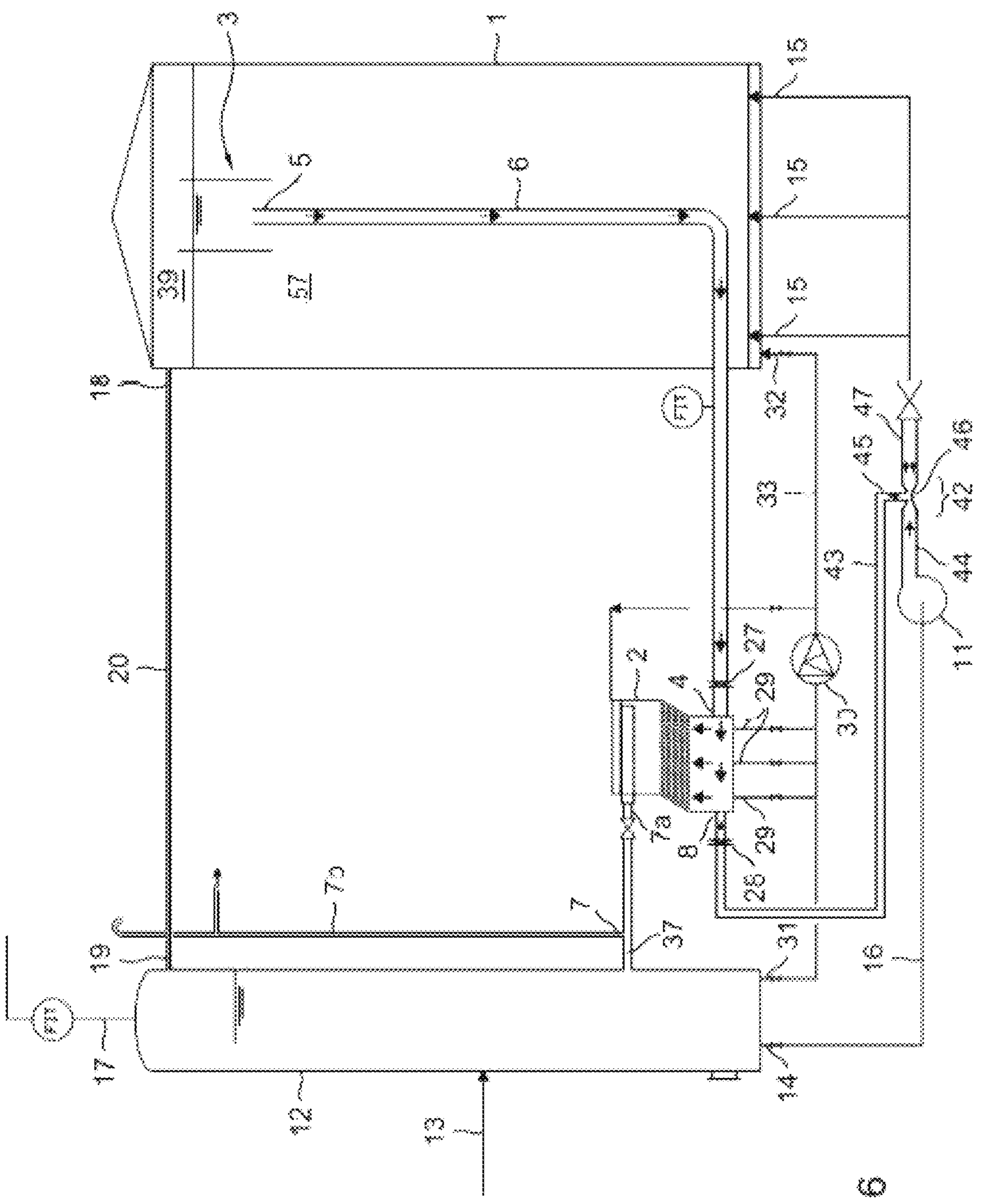
FIG. 6 schematically shows an installation according to the invention wherein use is made of the venturi-effect.

FIG. 6 schematically shows a design for an installation according to the invention wherein use is made of the venturi-effect. The higher pressure inlet side (44) of the venturi-injector (42) is connected with conduit 16 for aqueous fluid to be treated in the bioreactor (raw fluid or—as illustrated in FIG. 6—fluid from the conditioning tank 12), typically downstream of pump 11 (such that fluid enriched in biomass from the external separator (2) does not have to pass the pump). The suction inlet (45) in the constricted part of the venturi-injector is configured to allow fluid enriched in biomass from the external separator 2 via conduit 43 to be sucked into the flow path of the aqueous fluid that has entered the venturi-injector via higher pressure inlet side 44, whereby—during use—the aqueous fluid to be treated and fluid enriched in biomass from the external separator leave the venturi-injector (42) together via lower pressure outlet side 47 of the venturi-injector and are fed into the bioreactor (1) via inlet(s) 15.

Advantages of an embodiment wherein use is made of a venturi-effect include the simplicity of design. It omits the need of an injector for gas or pressurized liquefied medium or liquid containing dissolved gas which expands to generate a density reduction and biogas collectors (23), which facilitates revamping existing installations wherein the bioreactor is without biogas collectors (23), as the internal of the bioreactor does not have to be changed. An embodiment making use of the venturi principle can also be used in combination with an embodiment make use of the density reduction (such as a gas lift). It can e.g. be used when there is insufficient gas flow from the biogas collector (22) in the bioreactor or headspace (39) of the bioreactor to injector (23), for instance during start-up of the installation or if the collector becomes (partially) clogged or if biogas flow inside the bioreactor from underneath the collector into the collector is relatively low. The aqueous fluid treated in a method according to the invention can in principle be any aqueous fluid that comprises an organic substance that is biodegradable, in particular biodegradable under anaerobic conditions. Preferably, the aqueous fluid is selected from the group of municipal waste water, industrial waste water, sewage water, aqueous fluid waste from fermentation processes (such as residual fermentation broth), aqueous slurries and aqueous sludges. In terms of water content of a waste stream treated in a process according to the invention, this may vary in a wide range. Generally, the water content of the aqueous fluid to be treated is more than 80 wt. %, in particular at least 80 wt. %, more in particular 90 wt. % or more of the total weight of the fluid. Usually, the water content is 99.9 wt. % or less, preferably 99.5 wt. % or less, more preferably 99 wt. % or less, in particular 98 wt. % or less, more in particular 96 wt. % or less. The total organic substance content of the aqueous fluid to be fed into the bioreactor is usually 0.1 g COD/l or more, preferably in the range of 0.3-100 g COD/l, in particular in the range of 5-50 g COD/l.

Examples of aqueous fluids which are particularly suitable to be treated in accordance with the invention are aqueous wastes from a dairy food production or processing (e.g. the production/processing of milk, cheese, butter), a beverage production or processing (e.g. wine, beer, distilled beverage, fruit juice, milk), a biofuel or petrochemical production or processing, a chemical plant, an agricultural facility, a pulp and paper production or processing, a sugar processing or a yeast production.

Usually, a conditioning tank (12) is present in the installation in accordance with the invention. In such tank, during use, aqueous fluid that is to be subjected to a treatment in bioreactor is conditioned for the bioreactor. Advantageously, the conditioning tank is not only fed with aqueous fluid that has not been subjected to treatment in the bioreactor yet (raw aqueous feed), but it also receives part of the liquid phase (having reduced biomass content compared to the effluent of the bioreactor) leaving the external separator. This liquid phase is excellently suited to condition raw aqueous fluid that newly enters the installation.

An advantage of using the conditioning tank is that undesired fluctuations in the inflow of aqueous fluid into the bioreactor and undesired fluctuations in the quality of the aqueous fluid can be avoided. The recycle from separator to conditioning tank allows for a further improvement in maintaining a relatively constant flow in the various streams between different units of the installation, such as from the conditioning tank to the bioreactor and from bioreactor to external separator. It also offers further robustness, in allowing to keep fluid levels in the units relatively constant, also when there are large fluctuations in supply of aqueous fluid to be treated into the installation. Keeping flows into/from units relatively constant and/or fluid levels in units relatively constant by the recycle from separator to conditioning tank is desirable for efficient operation, but also for keeping the risk of, e.g., clogging of a conduit or clogging of the separator low.

Preferably, the raw aqueous fluid to be treated, such as raw wastewater, first enters the conditioning tank where specific parameters may be monitored such as temperature and/or pH. The skilled person will be able to determine favourable parameter values, dependent on the composition of the biomass. Usually the temperature of the contents of the conditioning tank are maintained at or adjusted to a temperature in the range of 20-55° C. Particularly good results have been achieved with a process wherein the aqueous fluid in the conditioning tank is maintained at or adjusted to a temperature in the range of about 30 to about 40° C., more in particular about 33 to about 37° C., e.g. in the range of 34 to 36° C. The pH of the contents of the conditioning tank is usually adjusted to or maintained at a pH in the range of about 6.0 to about 8.0, preferably in the range of 6.0-7.5, in particular of about 6.5 to about 7.2, e.g. in the range of 6.6 to 6.8. As the skilled person knows, for specific microbial cultures a different temperature or pH may be optimal. E.g., for alkaliphilic bacteria a higher pH may be favored, e.g. up to about pH 11.

The aqueous fluid, preferably after being pre-treated in the conditioning tank, is fed, preferably via an influent distribution system, adapted to provide an at least substantially equal distribution of the aqueous fluid over the horizontal cross section of the bioreactor, into a lower part of an upflow bioreactor where it passes upwards through a sludge bed, comprising biomass, preferably granular biomass.

The upflow bioreactor is preferably is a granular sludge bed, in particular an expanded granular sludge bed (EGSB), which (E)GSB comprises anaerobic microorganisms and wherein the biodegradable organic substance is converted by the anaerobic micro-organisms, thereby forming the biogas.

Suitable anaerobic micro-organisms are generally known in the art. Preferably the bioreactor comprises a consortium of microorganisms comprising at least one type of hydrolytic bacteria, at least one type of acidogenic bacteria, at least one type of acetogenic bacteria and at least one type of methanogenic bacteria.

Another factor that is relevant for good settleability of sludge, in particular of biomass granules—and thus good separation—is the height of the bioreactor where biomass is present. Typically, biogas can also occur in the inside of the granules, which may cause an upward flotation. At the bottom of the reactor the granules experience a higher pressure and thus biogas is released from the granule and settleability of the sludge is increased.

Preferably, an installation (for use in a process) comprises a bioreactor with a height ranging from about 15 to about 25 m, more preferably ranging from 18 to 22 m. Typically, the bioreactor is filled up to between 85-98 vol % with the aqueous fluid, preferably up to about 90-95 vol %.

Upon digestion of biodegradable organic substance in the bioreactor, a gas-aqueous fluid mixture is obtained.

The gas phase is comprised of biogas that is produced by the microorganisms. As is generally known, biogas generally at least substantially consists of methane and carbon dioxide, but additionally may also contain minor amounts of other gasses, such as hydrogen, ammonia, water vapor and/or hydrogen sulfide.

The aqueous fluid comprises solids, in particular biomass particles and optionally additionally include inorganic and/or organic suspended solids.

The aqueous fluid further comprises a liquid which usually essentially consists of water and water soluble substances such as organic acids and soluble substances that are not digested by microorganisms or other molecules that are typically present in water, such as minerals or salts.

The gas-aqueous fluid mixture moves upwards through the reactor where biogas separates from the mixture. This may either occur spontaneously or separation may be enhanced by internal separators.

The biogas leaves the bioreactor via a biogas outlet located at or near the top of the reactor (above the liquid level). It may leave the bioreactor directly, or may first enter into the upper part of the conditioning tank and exit the installation via an outlet located at or near the top of the tank. Optionally, the biogas is further treated in a manner known per se. The biogas may be used to provide energy for the process, i.e. to make the process self-sustainable, for example by heating the system. Alternatively, the biogas can be converted to electricity through a generator or upgraded to methane to be transported elsewhere to provide energy for other purposes or as a source for methane for use in a chemical process. As illustrated in FIG. 3, biogas from the headspace of the bioreactor may also be used to create or contribute to create a gas lift in the conduit (10) between external separator (2) and bioreactor (1).

In an advantageous embodiment, part of the biogas that is formed is transported from the bioreactor to a lower or middle part of the conditioning tank to improve the mixing of the aqueous fluid in the conditioning tank.

In an embodiment, the bioreactor additionally comprises an internal separator, wherein separation of biogas from an aqueous fluid comprising solids is promoted. If present, the internal separator is usually positioned in an upper part of the bioreactor. The internal separator preferably is a fluid-gas separator, more preferably a deflector or baffle located in an upper part of the bioreactor. The baffle or deflector is preferably located above the feed conduit to the external separator and promotes biogas separation from the aqueous fluid as a result of the natural upflow of biogas or biogas-fluid mixtures.

In an embodiment, the feed conduit to the external separator is an internal feed conduit. The internal feed conduit is for at least a substantial part located inside of the bioreactor. The inlet for collecting the aqueous fluid from which biogas has been separated is located under the baffle or deflector and collects the aqueous fluid which is then fed into the external separator.

In another embodiment, the feed conduit to the external separator is an external feed conduit. The inlet for the aqueous fluid is located on the side of the bioreactor and the external conduit to the external separator is located outside of the bioreactor. The bioreactor preferably comprises a baffle or deflector located near the external feed conduit inlet for directing the aqueous fluid into the external feed conduit, preferably located directly under the external feed conduit.

The internal or external feed conduit feeds the aqueous fluid into an external separator 2 comprising a separation chamber, typically provided with tilted internals for separating the aqueous fluid comprising biomass, and optionally other solids, into a liquid phase and a fluid phase enriched in biomass compared to the aqueous fluid entering the external separator.

In another embodiment, the internal separator is a funnel, preferably a mammoth pump funnel. If a funnel is present the lower part of the funnel is connected to the inlet of the internal feed conduit. The funnel promotes an efficient mammoth flow effect thereby aiding separation of biogas from the aqueous fluid (comprising liquids and solids) before the aqueous fluid enters the external separator. This gas-fluid separator mammoth pump funnel is preferably comprised by tilted walls shaped as a funnel towards bottom part connects an internal feed conduit.

In another embodiment, the internal separator is a gas-fluid separator comprising tilted internals, preferably tilted plates or tubes. Preferably, the gas-fluid separator is a tilted plate settler. The tilted plates cause turbulence inside of the separator, which aids the separation of biogas. The tilted plates can be flat or corrugated. Such tilted internals promote the separation of biogas from the fluid and solid phases. The tilted internals are usually placed at an angle of about 45-65°. Particularly good results have been achieved with placement at an angle of about 55 to about 60°. Adjacent internals are typically placed at a distance of at least 2 cm, in particular 2-10 cm distance from each other to enhance separation and avoid clogging of the separator. Preferably, the aqueous fluid enters the internal separator via the upper part of the separator. If a gas-fluid separator comprising tilted internals is present, the inlet of the internal feed conduit is connected to a lower part of the separator for collecting a fluid enriched in solids. The aqueous fluid comprising solids is typically collected at the bottom of the internal separator and fed into an external separator (2).

The external separator is typically configured such that, during use, the aqueous fluid comprising solids enters via an inlet located in a lower part of the separator. The external separator typically comprises tilted internals to enhance the settleability of the solid particles. The tilted plates can be flat or corrugated. Such tilted internals promote the separation of biogas from the liquid and solid phases due to a "lamella effect". The tilted internals are usually placed at an angle of about 45-65°. Particularly good results have been achieved with placement at an angle of about 55 to about 60°. Adjacent internals are typically placed at a distance of at least 2 cm, in particular 2-10 cm distance from each other to enhance separation and avoid clogging of the separator. from each other to enhance separation and avoid clogging of the separator. The use of tilted internals increases settling surface for the settling of solids.

The aqueous fluid passes upwards through the tilted internals where a laminar flow promotes the downward movement of solid particles, whilst allowing liquids to move into the upward direction, where an outlet for an aqueous fluid (effluent) is located.

The external separator preferably comprises isolation valves to allow for maintenance, replacement and repair of this module without affecting the reactor. Isolation of the external separator can also be used to provide regular cleaning in place of the external separator by isolating the device.

It is further preferred to have a conduit (33) connecting the external separator and the bioreactor and optionally the external separator and conditioning tank. This conduit further preferably has a pump (30), preferably a screw pump, for returning sludge to the bioreactor and to circulate chemicals through the external separator. These chemicals may be acidic or basic, depending on the impurity that needs to be removed. This pump allows cleaning in place of the external separator.

The external separator preferably has an elongated design.

The liquid phase that leaves the separator is usually at least substantially free of granular biomass. In an embodiment wherein the fluid that is fed into the separator contains suspended solids (in form of debris of granular biomass decay, flocculent—not granulated—biomass, and/or non-degradable suspended material), the liquid phase that leaves the separator will have a reduced suspended solids (particularly biomass content) compared to the fed fluid, but may contain residual flocculent biomass. If desired, this fluid can be purified in a manner known per se, e.g. if the liquid phase is to be taken from the installation to be discarded or put to further use, e.g. as process water. Liquid phase that is returned to the bioreactor, e.g. via the conditioning tank, can be returned without needing to remove these suspended solids.

Usually, the system according to the invention comprises a conditioning tank. If a conditioning tank is present, part of the liquid phase, obtained in the external separator may be returned to the conditioning tank to maintain the volume of fluid in the tank at approximately the same level.

The fluid phase enriched in biomass is re-entered into the bioreactor. It is desired for an efficient process to have a net growth of biomass during the process. During the start-up of the reactor, having a net growth of biomass in the system is important in order to obtain a sufficient amount of biomass for an efficient conversion of biodegradable substance. In a later stage of the process, having a net growth of biomass allows for extraction of sludge from the reactor without negatively affecting the turnover rate, i.e. the conversion of COD. In addition, having excess biomass additionally creates an increase in revenue, since the biomass can be easily stored, transported and sold.

As already explained above, in accordance with the present invention use is made of a density difference to create or contribute to a lift effect and/or use is made of the venturi-effect, which contribute(s) or create(s) a driving force for returning fluid enriched in biomass from the external separator to the bioreactor.

Using a density different to create or contribute to a lift effect and/or a venturi-effect advantageously allows omission of the use of a mechanical pump for returning the fluid enriched in biomass from the external separator to the bioreactor, for pro-longed periods of time. Hereby, biomass structure stability may be enhanced, and the risk of malfunctioning of the installation and energy of the method may be reduced. However, the installation (for use in a process) according to the invention, in addition to an injector configured to inject a fluid medium or a venturi-injector, optionally further comprises a mechanical pump configured to return a fluid enriched in biomass from the external separator to the bioreactor, typically provided in conduit (10). Said mechanical pump may serve as back-up means for returning the fluid enriched in biomass to the bioreactor. This mechanical pump is preferably used when the gas or venturi injector is temporarily not used, e.g. when the injector is under maintenance or otherwise out of order. This configuration allows for an optimal process in terms of efficiency, because during use, the method according to the invention may be continued when the injector is temporarily out of order. It was surprisingly found that such temporary use of a mechanical pump, preferably a use of between 1 hour to two weeks, such as between 12 hours and one week, in particular between 24 hours and 96 hours, did not have adverse effects to the structure of the granular biomass in the bioreactor.

Particularly good results have been achieved with making use of the density reduction to create a lift effect in the conduit returning the fluid enriched in biomass from external separator 2 to bioreactor 1 or in the bioreactor itself. Said density reduction is usually accomplished by injecting a fluid medium, such as a gas phase, a liquefied gas or a liquid comprising dissolved gas into the fluid enriched in biomass downstream of the external separator, typically in conduit (10). During use, the fluid medium is injected into the fluid enriched in biomass, typically into a conduit for fluids enriched in (granular) biomass (10) connecting the external separator (2) to the bioreactor (1), to promote the flow of the fluid enriched (granular) biomass from the external separator (2) towards the bioreactor (1). The gas is usually an inert gas, preferably nitrogen or a nitrogen-rich gas, such as air, or biogas. One or more components typically found in biogas, notably carbon dioxide, methane, may also be used.

Thus, in a preferred method one or more of the following feature apply:

- biogas is taken from the headspace of the bioreactor and introduced into said fluid phase enriched in biomass downstream of the external separator, thereby reducing the density of said fluid enriched in biomass downstream of the external separator (and creating or contributing to a gas lift);
- an external gas phase is introduced in said fluid phase enriched in biomass downstream of the external separator, thereby reducing the density of said fluid enriched in biomass downstream of the external separator (and creating or contributing to a gas lift) which gas preferably is an inert gas, such as nitrogen, or a nitrogen rich gas;
- a (pressurized) liquefied gas or a (pressurized) gas dissolved in a liquid phase is introduced in said fluid phase enriched in biomass downstream of the external separator, which liquefied gas or dissolved gas expands or evaporates (in the conduit returning the fluid phase enriched in biomass to the bioreactor or inside the bioreactor), thereby reducing the density of said fluid phase enriched in biomass downstream of the external separator;
- the density of said fluid phase enriched in biomass is reduced downstream of the external separator by 10-95%, preferably by 20-80%, in particular by 25-75%;
- the density of said fluid phase enriched in biomass is reduced downstream of the external separator to a density in the range of 10-900 $kg/m^3$, preferably to a density in the range of 100-850 $kg/m^3$, in particular to a density in the range of 200-800 $kg/m^3$, more in particular to a density in the range of 250-750 $kg/m^3$.

The 'external gas' is a gas which has not been produced in the installation comprising the bioreactor (used in) accordance with the invention, but supplied from a different source. The (pressurized) liquefied gas or a (pressurized) gas dissolved in a liquid phase may also be an external (pressurized) liquefied gas or a (pressurized) gas, although one may also use biogas produced in the installation (typically in the bioreactor) or a fraction thereof to provide pressurized) liquefied gas or a (pressurized) gas dissolved in a liquid phase.

Furthermore, once the aqueous fluid enriched in (granular) biomass of which the density has been reduced by introducing a gas phase in it, returns into the bioreactor (1), said gas phase promotes the upward flow of the aqueous fluid inside of the external separator (2), through a gas lift effect. Providing the fluid with the gas has as an additional advantage that clogging of the conduits is minimized, preferably prevented.

If the biogas for injection into the conduit (10) is collected from the bioreactor with a biogas collector, the biogas collector preferably has one or more biogas collector hoods, which is/are at least during use submerged in the fluid (suspension) in the bioreactor. If present, it is particularly preferred to have an internal biogas collector (22) positioned at a height whereby the biogas collector, at least during use of the installation, is submerged in the sludge bed in the bioreactor.

If present, preferably, the biogas collector hood(s) (22) is/are positioned below the inlet (9) for fluids enriched in (granular) biomass from the external separator (2).

If present, the biogas collector hood(s) (22) is/are preferably positioned below the inlet (5) of conduit (6) or inlet (35) of conduit (34) for the aqueous fluid for external separator (2).

However, in particular if an external gas, an external (pressurized) liquified gas or an external (pressurized) gas dissolved in a liquid phase, other than methane or a methane-rich gas, such as biogas, is used in accordance with the invention, it is preferred that said external gas or (pressurized) liquified gas is removed from the fluid enriched in biomass which has been subjected to a density reduction, for at least a substantial part, prior to returning said fluid to the bioreactor. Removal of said external gas, advantageously prevents the formation of a biogas-external gas mixture in the headspace of the bioreactor, thereby diluting the biogas fraction. The formation of such a biogas-external gas mixture is disadvantageous. In cases wherein the biogas is intended to be used as source of energy, formation of a biogas-external gas mixture is disadvantageous, because the energetic value of said biogas-external gas mixture would be lower than that of regular biogas produced in the bioreactor during use. In cases, wherein the biogas serves as a source for a starting material to synthesize other chemical products of interest, the dilution with another gas is also undesired as it may add an additional treatment to remove the gas before further processing of the biogas component of interest. Moreover, when a gas is used that comprises a substantial amount of oxygen, such as air, the risk exists of forming a potentially explosive mixture, unless precautions are taken to keep the oxygen content at a safe level. It should be noted that the presence of air in the fluid returned to the bioreactor as such is also acceptable for the microorganisms also for anaerobic micro-organisms (under essentially anaerobic conditions).

Accordingly, the invention further relates to an installation (for use in a process) according to the invention, wherein the injector configured to inject a fluid medium is connected to an external gas source (40), an external liquefied gas source or an external dissolved gas source, wherein the conduit (10) for returning a mixture of gas and the fluid enriched in biomass is provided with an outlet (52) connected to an inlet (51) of a fluid-gas separator (50) arranged to separate a gas phase from a fluid phase comprising biomass, wherein said fluid-gas separator (50) is provided with an outlet (53) configured to discharge gas from the gas-fluid separator and an outlet (54) configured to discharge a fluid comprising biomass into the bioreactor, which outlet (54) configured to discharge the fluid comprising biomass into the bioreactor is at a higher height than the injector configured to inject a fluid medium, and which outlet (54) configured to discharge the fluid comprising biomass into the bioreactor preferably is in a middle or lower part of the bioreactor. This is desired because it is advantageous to keep the solids content in the upper part of the bioreactor relatively low.

Said fluid-gas separator (50) is configured to separate the fluid into a gas phase and a fluid phase comprising biomass and is typically arranged relative to the bioreactor (1) such that, during use, the fluid level inside the fluid-gas separator (50) is at a higher level than the fluid level inside the bioreactor (1).

Any fluid-gas separators known in the art may be used to separate gas from the fluid enriched in biomass which has been subjected to a density reduction. Preferably, said fluid-gas separator is subjected to a gas-liquid separator, an air stripper or a gas separator drum.

A preferred example of a fluid-gas separator for use in an installation according to the invention is shown in FIG. 9. The fluid-gas separator (50) is connected to conduit (10) under an angle tau, which angle is preferably from 5 to 85°, more preferably from 40 to 80°, even more preferably from 60 to 75° relative to the vertical-axis. During use, such an angle advantageously allows efficient charge of the fluid enriched in biomass which has been subjected to a reduction in density into the fluid-gas separator (50), because it allows the use of gravity to transport the fluid comprising biomass into the fluid-gas separator. Hereby, the risk of clogging the conduit (10) is minimized.

Said conduit (10) is further configured to comprise an outlet (55) for gas, preferably said outlet is located in an upper part of said conduit for discharging gas, preferably air. This outlet (55) allows discharge of gas from conduit (10). Said outlet (55) is generally located at height h2, which is higher than the fluid level (during use) inside the bioreactor. The height h2 may be chosen within wide limits. The skilled person will be able to choose a suitable h2 based on the information disclosed herein and common generally knowledge. Suitable is for instance an h2 of 0.5 m or more in particular of 1.0 m or more, more in particular about 1.5 m or more. In embodiment, h2 is 10 m or less, in particular 5 m or less, more in particular about 2.5 m or less.

Further, said fluid-gas separator (50) is configured to comprise inlet (51) connected to an outlet of the conduit (10) for a fluid enriched in biomass and comprising gas is configured such that, during use, the fluid enriched in biomass and comprising gas enters the gas-fluid separator (50) at a position which is located at height h1, which h1 is higher than the fluid level inside the bioreactor (1). Preferably, the inlet is configured such that h1 is from 0.5 to 1.5 m higher than the fluid level inside the bioreactor, more preferably from 0.7 and 1.3 m higher. Good results were obtained with an h1 of about 1 m or more, because it allows sufficient phase separation of the fluid phase comprising biomass and the gas phase.

Said fluid-gas separator (50) is further provided with an outlet for gas (53) and an outlet for fluid enriched in biomass (54). The gas leaves the fluid-gas separator (50) via an outlet (55) located at or near the top of the fluid-gas separator (above the liquid level). It may leave the fluid-gas separator directly or it may be further treated in a manner known per se. The fluid enriched in solid leaves the fluid-gas separator in a lower part of the fluid-gas separator via conduit (10'). Preferably, said conduit 10' is essentially straight, i.e. essentially free of bends or kinks having an angle of less than 160°, preferably less than 180°, to avoid clogging or blockage due to accumulation of biomass into conduit 10'. As explained above, said outlet (54) configured to discharge the fluid comprising biomass into the bioreactor is at a higher height than the injector configured to inject a fluid medium. This is desired to benefit optimally from the gas lift effect provided by the injection of said fluid medium. Further outlet (54) is configured to discharge the fluid comprising biomass into the bioreactor preferably is in a middle or lower part of the bioreactor. This is advantageous because it is desired to keep the solids content in the upper part of the bioreactor relatively low.

The invention also relates to an apparatus, which apparatus is a separator (which may be used as an external separator in a method according to the invention or which may be an external separator of an installation according to the invention, in particular a settler, comprising a separation chamber provided with a modular tilted-internals unit and a sealable entry for the modular tilted-internals unit, such as a lid or removable flange, which entry allows replacement of the tilted internals or temporal removal, e.g. for maintenance of the separator. Such module may be a TPS module cassette. Thus internals can be replaced easily by a spare set of internals, with minimum down-time of the separator; also cleaning/maintenance of the remainder of the external separator is facilitated when internals can easily be taken out. The separator apparatus according to the invention usually is elongate, e.g. essentially cuboid or essentially cylindrical. The separator apparatus comprises an inlet for fluid to be subjected to a separation treatment, typically at or near one extremity (base side, 102*a*) of the separator into the separating chamber, which contains the internals-module (102*e*). The inlet preferably comprises and inlet distribution chamber. At least when in use the replaceable module (102*e*) comprising tilted separation internals are present at least substantially along the separation chamber, preferably along an at least essentially horizontal axis an outlet for fluid with reduced solids content (107*a*) and an outlet for fluid (sludge) with increased solids content (108) are generally provided at or near the extremity opposite to the inlet side. Generally, the outlet for fluid with reduced solids content (107*a*) will be positioned at least substantially above the internals, whereas the outlet for fluid (sludge) with increased solids content (108) will be positioned at least substantially below the internals.

In a preferred embodiment, the (external) separator apparatus according to the invention has an essentially cuboid shape, and contains a lid, e.g. a top lid or a side let along the length of the internals-module, via which the separation chamber can be opened and the internals-module can be removed.

Figure 7:
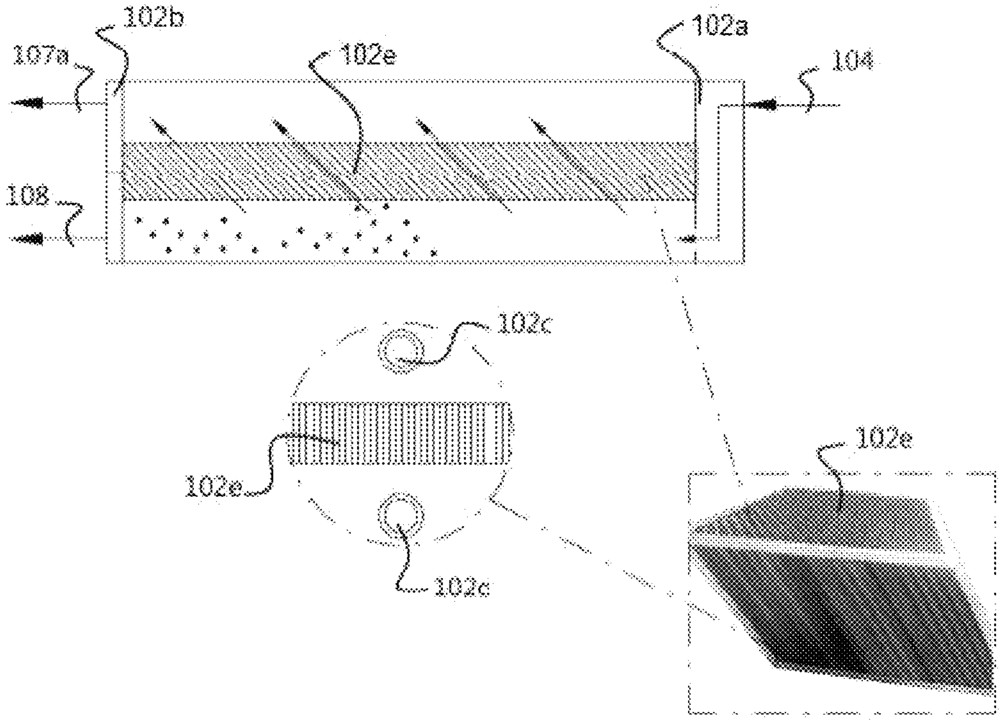
FIG. 7 schematically shows an embodiment of the installation that includes a separation chamber.

In a further preferred embodiment, as schematically shown in FIG. 7, the (external) separator apparatus according to the invention has a separation chamber having an at least substantially round cylindrical shape, wherein a module (102*e*) is present comprising the tilted internals.

The inventor realized that at least substantially round cylindrical design wherein the modular internals are adapted to be replaceable from the separation chamber via at least one of the base sides which is openable and closable is particularly advantageous, not only because it facilitates repair/maintenance, but also because such design facilitates having a openable/closable separator that can withstand pressures advantageously applied to the separation chamber (typically up to about 2.5 bar).

Thus, in an advantageous embodiment, the separator comprises an at least substantially round-cylindrical separation chamber, which is—during use—positioned essentially horizontally (i.e. its radial axis is essentially horizontal), in which separation chamber—at least when in use—a replaceable module (102*e*) comprising tilted separation internals are present at least substantially along the separation chamber's radial axis, and which separation chamber has at least one base side (102*a*, 102*b*) which is sealable and openable to provide and opening adapted to allow placing the module comprising tilted separation internals into its working position and removing it from its working position. E.g. flanges (102*c*, 102*d*) may be provided at the sealable and openable base-side(s). In FIG. 7 the inlet (104) for fluid comprising solids to be treated is schematically shown at the right side arrow). In use, the fluid preferably enters the separator via an inlet distribution chamber and then flows into the separation chamber. The separator further comprises an outlet for fluid with reduced solids content (107*a*) is shown at the left side upper arrow and an outlet for fluid (sludge) with increased solids content (108) at the left side lower arrow.

In a particularly advantageous embodiment, the (external) separator apparatus according to the invention, respectively the external separator of an installation according to the invention or used in a method according to the invention comprises an at least substantially cuboid or an at least substantially round-cylindrical separation chamber, which is—during use—positioned essentially horizontally (i.e. its radial axis is essentially horizontal), in which separation chamber a tilted-separation-internals module is present at least substantially along its radial axis, an inlet configured for feeding the aqueous fluid comprising solids (such as biomass from the bioreactor) into a lower part of the external separator, below the internals, a passage way for the aqueous fluid comprising solids from the inlet through the internals towards a first outlet for an aqueous fluid having a reduced solids content positioned at least substantially above the internals and a second outlet for an aqueous fluid enriched in solids (sludge) positioned at least substantially below the internals.

In an installation for use in accordance with the invention, the inlet of the external separator is typically connected to the inlet (5) of the internal feed conduit (6) or the inlet (35) of the external feed conduit (34). During use the aqueous fluid is separated into a liquid phase and a fluid phase enriched in granular (granular). The external separator further comprises an outlet (8) for returning an aqueous fluid enriched in (granular) biomass to the bioreactor, which is connected to in inlet (9) for an aqueous fluid enriched in (granular) biomass of the bioreactor via a conduit (10). Conduit (10) is equipped with a biogas injector (23) for injecting biogas into the fluid enriched in (granular) biomass, which biogas injector is connected to a biogas collector (22) via a conduit (21).

It is possible that during start-up of the reactor the biogas production is not yet sufficient to cause a sufficient upward flow withdrawing a fluid enriched in (granular) biomass from the external separator into the bioreactor without mechanical assistance or use of an external gas source. In such a case mechanical assistance such as a recirculation pump may be present to draw said fluid comprising biomass from the external separator into the bioreactor. Furthermore, the presence of such a pump minimizes or prevents clogging of the conduits as a result of sedimentation of sludge in the lines.

Preferably, a conditioning tank (12) is present from which, during use, aqueous fluid is supplied into the bioreactor. To improve mixing of the aqueous fluid which is present in the conditioning tank, a biogas conduit is preferably provided that introduces biogas from the bioreactor into the conditioning tank.

Preferably a recirculation pump is used to generate sufficient upward flow to draw the settled solids from the external separator into the bioreactor.

The external separator is placed outside of the bioreactor to improve accessibility, thereby facilitating maintenance and start-up procedures and further enables the installation of the reactor in parts, i.e. allowing for an already existing system to be upgraded with an external settler, thereby improving the efficiency of the reactor.

Preferably, conduits connecting the external separator with other parts of the installation comprise isolation valves, allowing for the isolation of the external separator and thus facilitating cleaning in place or maintenance of the external separator. Further, because the external separator is usually placed lower than the inlet of the feed conduit for the external separator, the pressure in the external separator is higher than the pressure in the upper part of bioreactor. Typically the difference in pressure is between about 1.5-3 bars. The higher pressure compresses the biomass granules thereby removing possible gas that is still present inside of the granule and thus enhancing the settleability of the granules and thus improving removal of solids from the liquid phase.

As already explained in detail above, at least part of the driving force for the recycle fluid phase enriched in biomass from the external separator to the bioreactor makes use of a gas-lift principle. In order to use this principle, the external separator is preferably placed sufficiently low to allow the recycle conduit (10) to extend upward enough to create the gas lift, And return the fluid phase enriched in biomass into a middle or lower part of the bioreactor. This is desired because it is desired to keep the solids content in the upper part of the bioreactor relatively low. Accordingly, the external separator is advantageously positioned at or near the floor of the installation or at about the same height or below the bottom of the bioreactor, whilst the inlet (9) for the recycled fluid enriched in biomass into the bioreactor (1) via conduit (10) is positioned at a higher level than at least the outlet (29) of fluid enriched in biomass of the external separator, and preferably from at a higher level than the top of the external separator. Satisfactory height differences between the outlet (29) of fluid enriched in biomass of the external separator, the gas injector (23) into the recycle conduit (10) and the inlet (9) for recycled fluid enriched in biomass from the external separator can be based on the information disclosed herein, common general knowledge and optionally a limited amount of routine trial and error. In particular, the skilled person will be able to choose height differences such that the pressure differences are such that they drive the fluids/solids/gas in the right direction.

In a specific embodiment, the conduit for feeding an aqueous fluid from the bioreactor to the external separator is at least substantially straight, i.e. does not contain sharp angles or sharp edges, to prevent sludge from precipitating the conduits, leading to clogging of the system.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

The term "(at least) substantial(ly)" is generally used herein to indicate that it has the general character or function of that which is specified. When referring to a quantifiable feature, this term is in particular used to indicate that it is at least 50%, more in particular more than 75%, even more in particular more than 90% of the maximum of that feature. The term 'essentially free' is generally used herein to indicate that a substance is not present (below the detection limit achievable with analytical technology as available on the effective filing date) or present in such a low amount that it does not significantly affect the property of the product that is essentially free of said substance. In practice, in quantitative terms, a product is usually considered essentially free of a substance, if the content of the substance is 0-1 wt. %, in particular 0-0.5 wt. %, more in particular 0-0.1 wt. %.

In the context of this application, the term "about" means generally a deviation of 15% or less from the given value, in particular a deviation of 10% or less, more in particular a deviation of 5% or less.

As used herein "biodegradable organic substance" is organic substance that can be converted by biomass in the reactor, typically under essentially anaerobic conditions, in particular into biomass or methane.

The term "fluid" is used herein for liquids and mixtures of liquids and at least one other phase, such as suspensions, that flow without applying external pressure (pressure other than gravity).

The term "liquid" is used herein for an aqueous fluid that is essentially free of particles that are visible with the naked eye, i.e. with a size <0.1 mm.

As used herein "organic substance' is any organic substance that is chemically oxidisable, as can be determined by the Chemical Oxygen Demand (COD) test, as described in ISO 6060:1989. A content of organic substance is generally expressed in g COD, i.e. grams oxygen that is consumed for the oxidation of the organic substance.

The skilled person is familiar with terms like 'upper', 'lower', 'middle', 'at bottom', 'near bottom', 'at top' and 'near top'. Generally these are read in relation to another, and the skilled person will be able to reduce implementation thereof to practice, based on common general knowledge, the information and citation disclosed herein, and the specifics of a unit (such as bioreactor, a separate container, or a volume of matter contained in the bioreactor or a section) of the installation.

As a rule of thumb, unless follows differently from the context, 'near' a certain reference point (such as 'bottom' or 'top') usually means 'at a relative height of up to +/−20%' from the reference point', in particular s 'at a relative height of up to +/−15%' from the reference point' more in particular 'at a relative height of up to +/−10%' from the reference point. The relative height is the distance from the bottom divided between the total height of the unit (height difference between bottom and top).

As a rule of thumb, unless follows differently from the context, an 'upper' part generally means in the upper ½, and in particular in the upper ⅓ of the unit, a 'lower' part generally means the lower ½ of the unit and in particular the lower ⅓ of the unit. When referring to a middle part, this in particular means the middle ⅓ of the unit (from ⅓ of the bottom to ⅓ from the top).

For the purpose of clarity and a concise description, features are described herein as part of the same or separate embodiments, however, it will be appreciated that the scope of the invention may include embodiments having combinations of all or some of the features described.

Legend to the Figures: (1) bioreactor; (2) external separator; (3) internal baffle or deflector/separator; (4) inlet of external separator for an aqueous fluid; (5) inlet of a conduit (6) for withdrawing an aqueous fluid from bioreactor (1); (7*a*) outlet of external separator for aqueous fluid; (8) an outlet for a fluid enriched in biomass; (9) inlet for the fluid enriched in biomass into the bioreactor (1); (10) conduit for fluid enriched in biomass which has been subjected to a reduction in density; (11) mechanical pump; (12) conditioning tank; (13) inlet for wastewater; (14) outlet for the aqueous fluid; (15) inlet of the bioreactor for aqueous fluid from the conditioning tank; (16) conduit for aqueous fluid to the bioreactor; (17) outlet for biogas from the conditioning tank; (18) outlet for biogas from the bioreactor; (19) inlet for biogas from the conditioning tank; (20) conduit for biogas; (21) biogas conduit; (21) biogas injector; (22) biogas collection hoods; (23) biogas injector; (24) T-junction for connecting the biogas conduit (21) to the biogas conduit (26) for introducing biogas; (25) inlet of the conditioning tank; (26) biogas conduit); (27) valve; (28) valve; (29) inlets/outlets connected to the inlet/outlet (31) of the conditioning tank; (30) pump for returning sludge from the external separator to the bioreactor; (32) inlet of the bioreactor; (33) conduit for returning sludge to the bioreactor; (34) feed conduit configured to feed aqueous fluid comprising solids from the bioreactor into the external separator; (35) outlet of the bioreactor located above (36) a deflector or baffle; (37) return line for liquid phase from the external separator to the conditioning tank; (38) gas conduit from (39) the headspace of the bioreactor to the gas injector; (40) external gas source; (41) conduit for external gas; (42) venturi-injector; (43) conduit for fluid enriched in biomass to be sucked into the flow path of the aqueous fluid that has entered the venturi-injector via higher pressure inlet side (44); (45) suction inlet; (47) lower pressure outlet of the venturi-injector; (50) gas-fluid separator; (51) inlet of gas-fluid separator for fluid enriched in biomass that has been subjected to a density reduction; (52) outlet of conduit (10) for fluid enriched in biomass that has been subjected to a density reduction; (53) outlet of the gas-fluid separator for discharging gas; (54) outlet of the gas-fluid separator for discharging a fluid enriched in biomass; (55) outlet for discharging gas; (102*a*, 102*b*) base side of the separator; (102*c*, 102*d*) flanges; (102*e*) replaceable module comprising tilted separation internals; (104) inlet for fluid comprising solids to be treated; (107*a*) outlet for fluid with reduced solids content; (108) an outlet for fluid (sludge) with increased solids content.

EXAMPLE

Waste water from the pulp and paper industry was treated in an installation according to the invention (see e.g. FIGS.

3 and 4). During two time intervals, respectively of 50 days and 150 days, two different means of reducing the density of the fluid enriched in biomass downstream of the external separator were utilized and compared in terms of velocity turnover rate (VLR).

During the first fifty day time interval, waste water was treated in an installation according to the invention, wherein biogas was collected inside the bioreactor using collection hoods and subsequently introduced into the fluid phase enriched in biomass downstream of the external separator.

After fifty days, the density of the fluid enriched in biomass downstream of the external separator was reduced by introducing air, using a mechanical pump or compressor, into the fluid enriched in biomass, downstream of the external separator. The waste water was treated for another 150 days.

Figure 10:
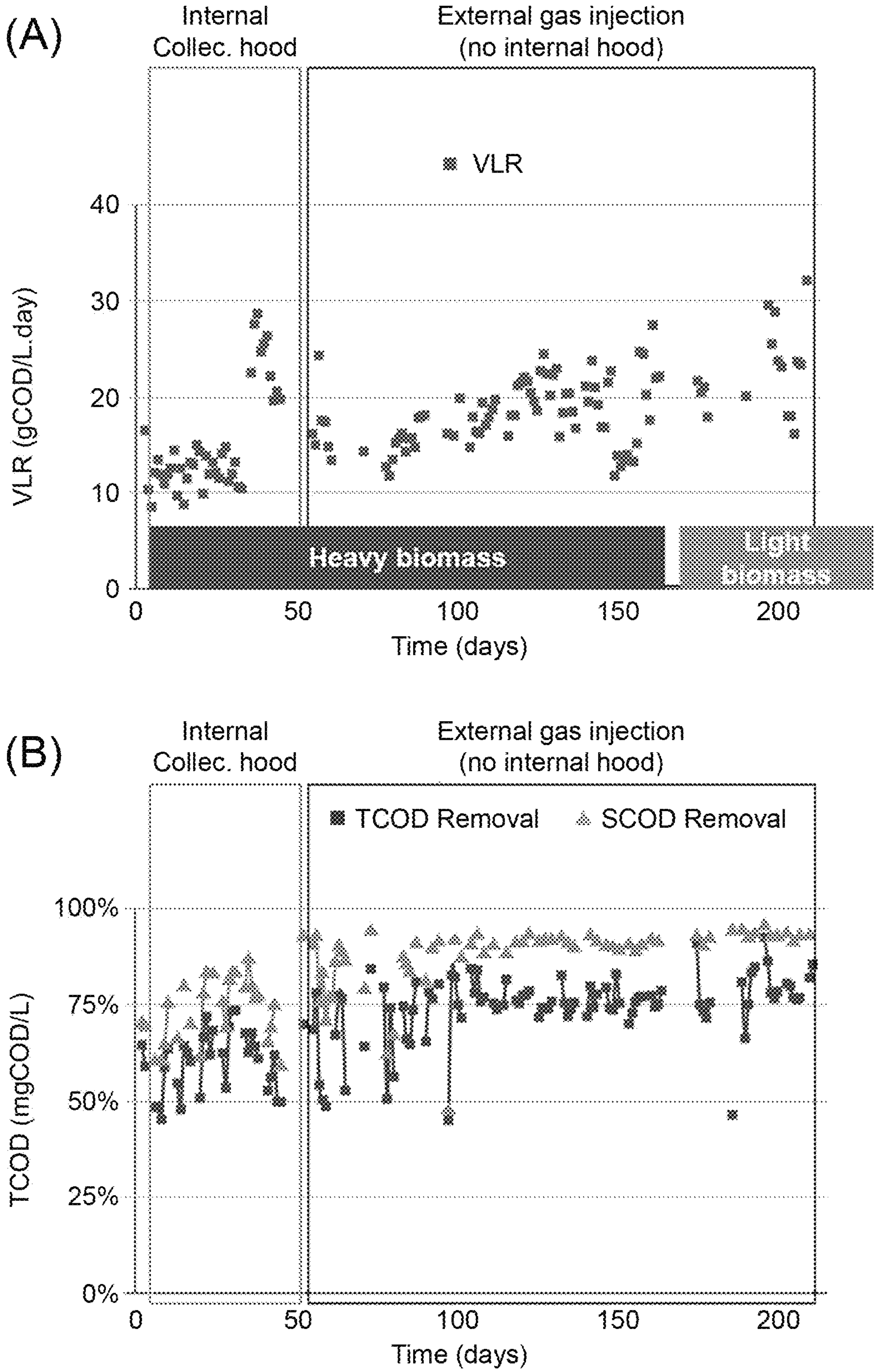
FIG. 10A is a graph showing the change in the volumetric loading rates of an aqueous fluid treated over a period of days.
FIG. 10B is a graph showing the Chemical Oxygen Demand removal over a 200 day period.

The volumetric loading rates (VLR) and the average total COD (tCOD) and soluble COD (sCOD) of the effluent stream over the whole treatment duration were determined during the whole treatment duration. The results are shown in FIG. 10 and Table 1.

As shown in FIG. 10A, a VLR of between 10-30 kg COD/L day was achieved during the first fifty days of treatment, wherein the fluid enriched in biomass downstream of the external separator was subjected to a density reduction by introducing biogas collected in the bioreactor using collection hoods, into said fluid. Further, a slightly higher VLR was obtained when using external gas to reduce the density of the fluid enriched in biomass downstream of the external separator. It is further shown in FIG. 10A that the VLR shows fewer variations, e.g. is more stable when the density of the fluid enriched in biomass downstream of the external separator was reduced using an external gas, compared to using biogas collected with biogas hoods inside the bioreactor. The process was stable and no operational issues were observed during the processing times of at least 200 days.

Furthermore, as can be derived from Table 1 and FIG. 10B, an average of sCOD removal rate of more than 92% and an average of tCOD of more than 80% was achieved.

TABLE 1

Biomass content in the bioreactor, external separator and effluent line. Average values shown between brackets.

| Biomass | Bioreactor Volumetric loading rate (VLR) kgCOD/m3 d) | External separator "settler load" (horizontal cross section velocity) m/h | Effluent Granular biomass Imhoff Ml/L |
|---|---|---|---|
| Heavy (45% Volatile Solids (VS)) | 16-24 (20) | 16-31 (21) | 0.1-4.0 (1.4) |
| Light (80% VS) | 16-32 (24) | 19-28 (24) | 0.5-1.4 (1.3) |

As can be derived from Table 1 and FIG. 10A, a VLR of 16-24 kg COD/m3 day could be achieved with the process according to the invention. This performance is comparable to the performance of a regular EGSB. In addition, as shown in Table 1 with the method according to the invention, a settler cross section velocity could be achieved of 16-31 m/hr. This velocity is much higher compared to a conventional EGBS, wherein cross section velocities typically range between 10-12.5 m/h, hence improving the efficiency of the process. This means that, in order to achieve the same velocity as achieved in a EGBS, a settling area that is around 1.5 to 3 times smaller may be employed. This renders the installation much more compact.

Further, as can be derived from Table 1, the concentration of biomass in the effluent was consistently below 5 mL of biomass per L of effluent, and on average below 1.5 mL of biomass per L of effluent. These results confirm that the separation efficiency of the method according to the invention is outstanding.

Figure 11:
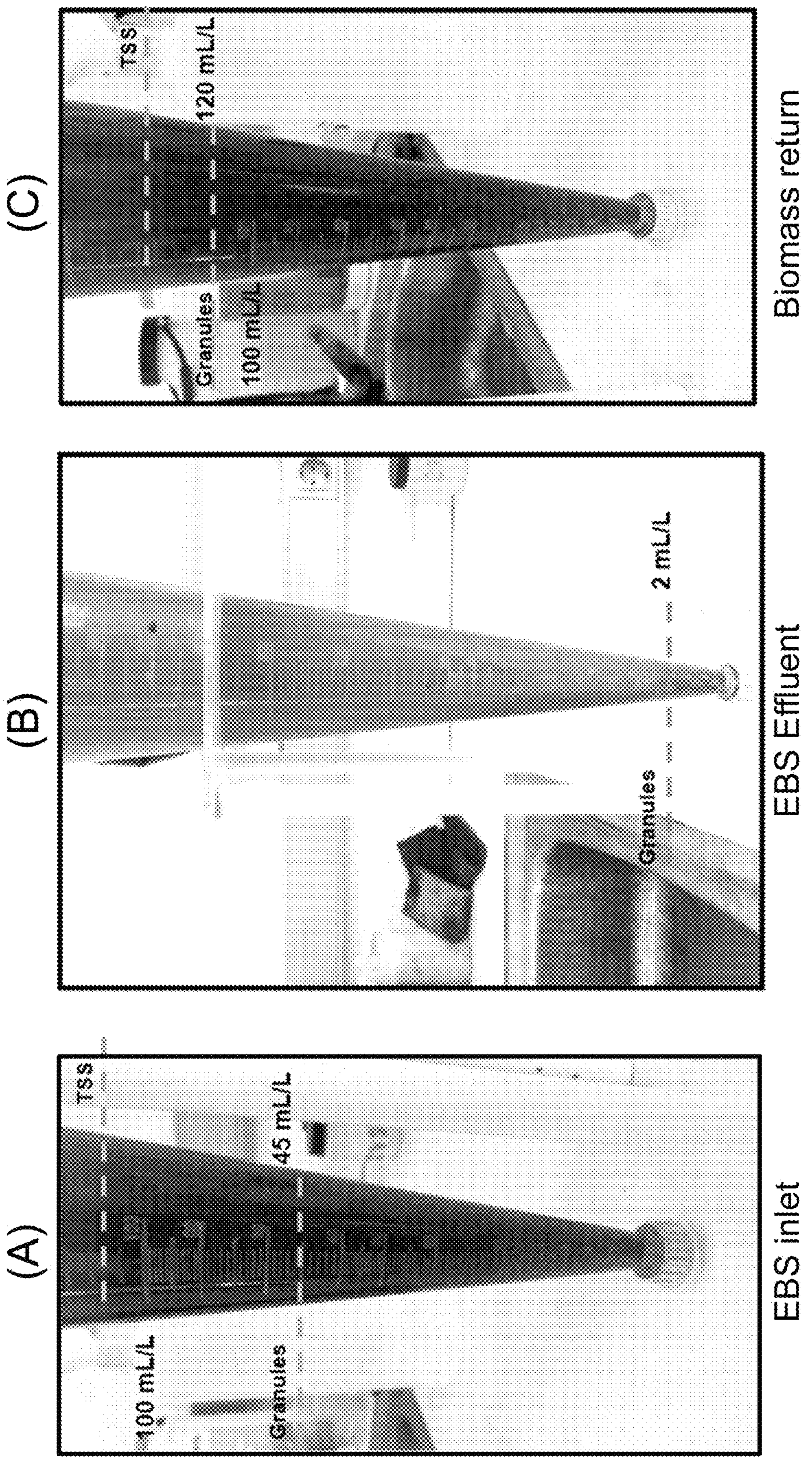
FIG. 11A-C show the biomass content of the inlet of the external separator, the effluent, and the biomass return line, respectively.

The excellent separation efficiency is also in FIG. 11, showing that the effluent has been substantially purified, having a biomass content of 2 ml/L (FIG. 11B). This is much lower compared to samples taken at the inlet of the external separator, where a biomass content of 45 ml/L was measured (FIG. 11A) and from the biomass return line, showing a biomass content of around 100 ml/L (FIG. 11C).

It can be concluded from the results that the method according to the invention allows treatment of waste water at both high efficiency, as reflected in the high VLR's and in high purity, as reflected in the excellent COD removal.

The invention claimed is:

1. A method for treating an aqueous fluid comprising a biodegradable organic substance in an installation comprising an upflow bioreactor containing a sludge bed, said sludge bed comprising biomass and an external separator, wherein the method comprises:

feeding the aqueous fluid into a lower part of the bioreactor, contacting the fed fluid with the biomass, thereby forming biogas from the biodegradable organic substance;

withdrawing the fluid that has been contacted with the biomass from an upper part of the bioreactor, which withdrawn fluid comprises biomass;

feeding the fluid comprising the biomass withdrawn from the upper part of the bioreactor into the external separator comprising a separation chamber, wherein the fluid comprising the biomass is separated into a liquid phase, which has a reduced biomass content or is essentially free of biomass, and a fluid phase enriched in biomass and having a density;

subjecting the fluid phase enriched in biomass to a density reduction downstream of the external separator to provide a fluid phase enriched in biomass having a reduced density, wherein the density reduction is accomplished by introducing an external gas in said fluid phase enriched in biomass; and returning the fluid enriched in biomass which has been subjected to said density reduction to the bioreactor.

2. The method according to claim 1, wherein the bioreactor has a headspace, and wherein biogas is taken from the headspace of the bioreactor and introduced into said fluid phase enriched in biomass downstream of the external separator, thereby reducing the density of said fluid enriched in biomass downstream of the external separator.

3. The method according to claim 1, wherein the external gas is a pressurized liquefied gas or a pressurized gas dissolved in a liquid phase, which thereby reducing the density of said fluid phase enriched in biomass downstream of the external separator.

4. The method according to claim 1, wherein said fluid enriched in biomass which has been subjected to said density reduction is fed into a gas-fluid separator, wherein the fluid is separated into a gas phase and a fluid phase comprising biomass, and wherein said fluid phase comprising biomass is returned to the bioreactor.

5. The method according to claim 4, wherein the gas-fluid separator is a gas-liquid separator, an air stripper or a gas separator drum.

6. The method according to claim 1, wherein the density of said fluid phase enriched in biomass is reduced downstream of the external separator by at least 10%.

7. The method according to claim 1, wherein the installation comprises a conditioning tank into which the aqueous fluid to be treated in the bioreactor is fed, from which conditioning tank the aqueous fluid is fed to the bioreactor and wherein a part of the liquid phase having a reduced biomass content or being essentially free of biomass is fed from the external separator to said conditioning tank.

8. The method according to claim 1, wherein the bioreactor comprises a granular sludge bed (GSB), which GSB comprises anaerobic microorganisms and wherein the biodegradable organic substance is converted by the anaerobic micro-organisms, thereby forming the biogas.

9. The method according to claim 1, wherein the fluid that is withdrawn from the upper part of the bioreactor comprises granular biomass, wherein granular biomass settles inside the external separator, and wherein the fluid phase that is returned to the bioreactor comprises settled granular biomass.

10. The method according to claim 1, wherein the external separator is placed lower in elevation than the inlet withdrawing aqueous fluid from the bioreactor of the feed conduit feeding said fluid to the external separator.

11. The method according to claim 1, wherein the external gas is air.

12. The method according to claim 1, wherein the external gas is nitrogen.

13. An installation for microbiologically treating an aqueous fluid comprising a biodegradable organic substance, wherein the installation comprises:

an upflow bioreactor, the bioreactor comprising a sludge bed and an outlet for biogas;

an external separator comprising a separation chamber arranged to separate a liquid phase from a fluid phase comprising biomass, the external separator comprising an inlet for an aqueous fluid connected to an inlet of a conduit for withdrawing an aqueous fluid from the bioreactor, an outlet for aqueous fluid, an outlet for a fluid enriched in biomass connected to the bioreactor via a conduit; and at least one injector selected from the group consisting of:

(a) one or more injectors configured to inject a fluid medium comprising a gas or a pressurized liquid into the fluid enriched in biomass downstream of the external separator into the conduit connecting the outlet of the fluid enriched in biomass and the bioreactor to form a mixture, and (b) one or more venturi-injectors configured to return fluid enriched in biomass from the external separator to the bioreactor, wherein said at least one injector configured to inject a fluid medium is connected to an external gas source, an external liquefied gas source or an external dissolved gas source.

14. The installation according to claim 13, wherein the bioreactor has a headspace, and a conduit providing a flow path for biogas from said headspace to said at least one injector configured to inject a fluid medium, and wherein the conduit returns a mixture of the fluid phase enriched in biomass and the biogas that has been injected in said fluid phase.

15. The installation according to claim 13, wherein the conduit between outlet for a fluid enriched in biomass of the external separator and inlet for returning the fluid enriched in biomass into the bioreactor is provided with an outlet connected to an inlet of a fluid-gas separator arranged to separate a gas phase from a fluid phase comprising biomass, wherein said fluid-gas separator is provided with an outlet configured to discharge gas from the gas-fluid separator and an outlet configured to discharge a fluid comprising biomass into the bioreactor, which outlet configured to discharge the fluid comprising biomass into the bioreactor is at a higher height than the injector configured to inject a fluid medium.

16. The installation according to claim 15, wherein the fluid-gas separator is arranged relative to the bioreactor such that, during use, the fluid level inside the fluid-gas separator is at a higher level than the fluid level inside the bioreactor.

17. The installation according to claim 13 for group (a), wherein the conduit for the mixture of the fluid medium and the fluid enriched in biomass is discharged into the bioreactor at a higher height than the one or more injectors.

18. The installation according to claim 13, comprising a conditioning tank for pretreating the aqueous fluid, comprising an inlet for wastewater, an outlet for the aqueous fluid connected to an inlet of the bioreactor via a conduit a return line for liquid phase from the external separator to the conditioning tank, and an outlet for biogas.

19. The installation according claim 13, wherein the bioreactor further comprises:

an internal biogas collector positioned at a height whereby the biogas collector, at least during use of the installation, is submerged in the sludge bed in the bioreactor, wherein the biogas collector is connected to the one or more venturi-injectors configured to inject biogas into the conduit for returning the fluid enriched in solids from the external separator to the bioreactor.

20. The installation according to claim 13, wherein the external separator is positioned at about the same height or below the bottom of the bioreactor.

21. The installation according to claim 13, wherein the installation comprises a feed conduit configured to feed aqueous fluid comprising solids from the bioreactor into the external separator, wherein the feed conduit has an inlet located above a deflector or baffle present in the bioreactor, which deflector or baffle is configured to direct aqueous fluid comprising solids present in the bioreactor into the feed conduit.

22. The installation according to claim 13, wherein the external separator comprises a separation chamber provided with a modular tilted-internals unit and a sealable and openable entry configured to allow replacement of the modular tilted-internals unit.

23. The installation according to claim 22, wherein the separation chamber is an at least substantially round-cylindrical separation chamber having a radial axis, which during use is positioned with the radial axis essentially horizontal, in which separation chamber—at least when in use—a replaceable module comprising tilted separation internals is present at least substantially along the separation chamber's radial axis, and which separation chamber has at least one base side which is sealable and openable to provide an opening adapted to allow placement of the module comprising tilted separation internals into its working position and removing it from its working position.

* * * * *